US010588600B2

(12) United States Patent
Arai et al.

(10) Patent No.: US 10,588,600 B2
(45) Date of Patent: Mar. 17, 2020

(54) ACOUSTIC MATCHING MEMBER, ACOUSTIC MATCHING MEMBER GROUP, AND MEDICAL IMAGING APPARATUS

(71) Applicant: FUJIFILM CORPORATION, Minato-ku, Tokyo (JP)

(72) Inventors: Takahisa Arai, Kanagawa (JP); Takeyasu Kobayashi, Kanagawa (JP); Takao Kuwabara, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 340 days.

(21) Appl. No.: 15/473,611

(22) Filed: Mar. 30, 2017

(65) Prior Publication Data
US 2017/0281124 A1 Oct. 5, 2017

(30) Foreign Application Priority Data

Apr. 1, 2016 (JP) ................................. 2016-074328

(51) Int. Cl.
*A61B 8/00* (2006.01)
*A61B 8/08* (2006.01)
*A61B 6/00* (2006.01)
*A61B 6/04* (2006.01)

(52) U.S. Cl.
CPC ............ *A61B 8/429* (2013.01); *A61B 6/0414* (2013.01); *A61B 6/4417* (2013.01); *A61B 6/502* (2013.01); *A61B 8/0825* (2013.01); *A61B 8/403* (2013.01); *A61B 8/4281* (2013.01)

(58) Field of Classification Search
CPC ..... A61B 8/429; A61B 8/4281; A61B 6/4417; A61B 6/0414; A61B 8/403; A61B 8/0825; A61B 6/502
See application file for complete search history.

(56) References Cited

U.S. PATENT DOCUMENTS

| 8,747,317 B2* | 6/2014 | Yu ........................ A61B 8/0825 600/437 |
| 9,823,182 B2* | 11/2017 | Suzuki ................ A61B 5/0091 |
| 2007/0058774 A1* | 3/2007 | Ramsauer ............. A61B 6/107 378/37 |
| 2008/0043904 A1* | 2/2008 | Hoernig ............... A61B 6/0414 378/37 |
| 2010/0290585 A1* | 11/2010 | Eliasson ................ A61B 6/025 378/37 |
| 2012/0051501 A1* | 3/2012 | Nakayama ............... A61B 6/00 378/37 |
| 2012/0114095 A1* | 5/2012 | Smith .................... A61B 6/025 378/20 |

(Continued)

FOREIGN PATENT DOCUMENTS

JP 2005-270677 A 10/2005

*Primary Examiner* — Sanjay Cattungal
(74) *Attorney, Agent, or Firm* — Solaris Intellectual Property Group, PLLC

(57) ABSTRACT

An acoustic matching member configured to be disposed between a breast placed on an imaging table and a compression plate disposed opposite to the imaging table is proposed. The acoustic matching member includes a protruding portion that protrudes toward the imaging table and that is provided in an end portion on a deepest side when viewed from a chest wall side of a subject in a case of compressing a breast of the subject in contact with the compression plate.

11 Claims, 16 Drawing Sheets

(56) References Cited

U.S. PATENT DOCUMENTS

| | | | |
|---|---|---|---|
| 2012/0238859 A1* | 9/2012 | Tokita | A61B 5/0095 600/407 |
| 2013/0281840 A1* | 10/2013 | Vaughan | A61B 6/0414 600/425 |
| 2015/0335252 A1* | 11/2015 | Hirota | A61B 5/0095 600/407 |
| 2016/0007961 A1* | 1/2016 | Lee | A61B 8/4494 600/459 |
| 2016/0242709 A1* | 8/2016 | Radicke | A61B 6/025 |
| 2016/0256125 A1* | 9/2016 | Smith | A61B 6/025 |
| 2017/0188874 A1* | 7/2017 | Suhami | A61B 5/0507 |

* cited by examiner

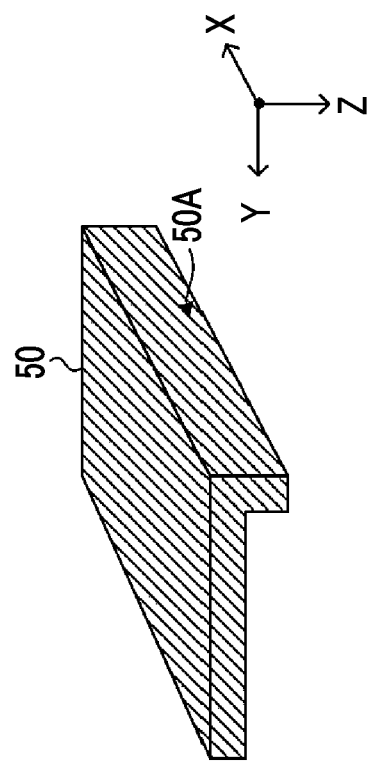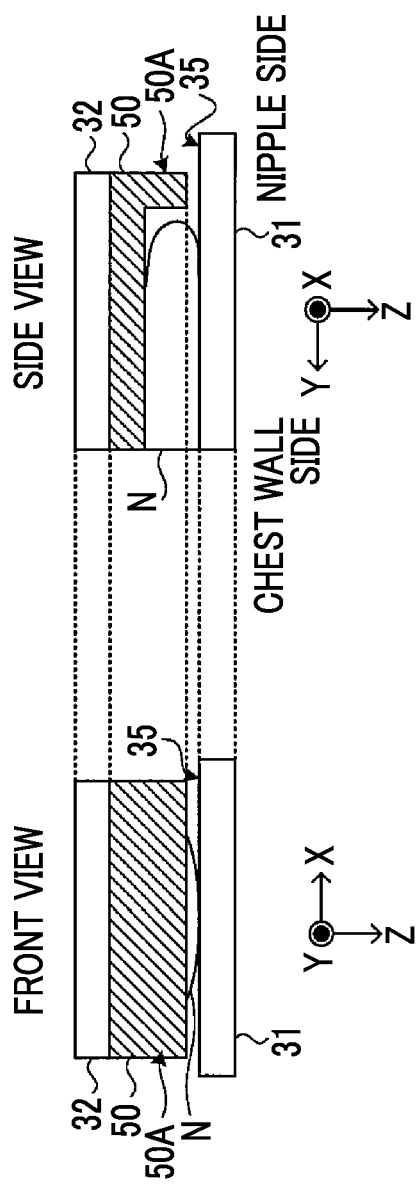

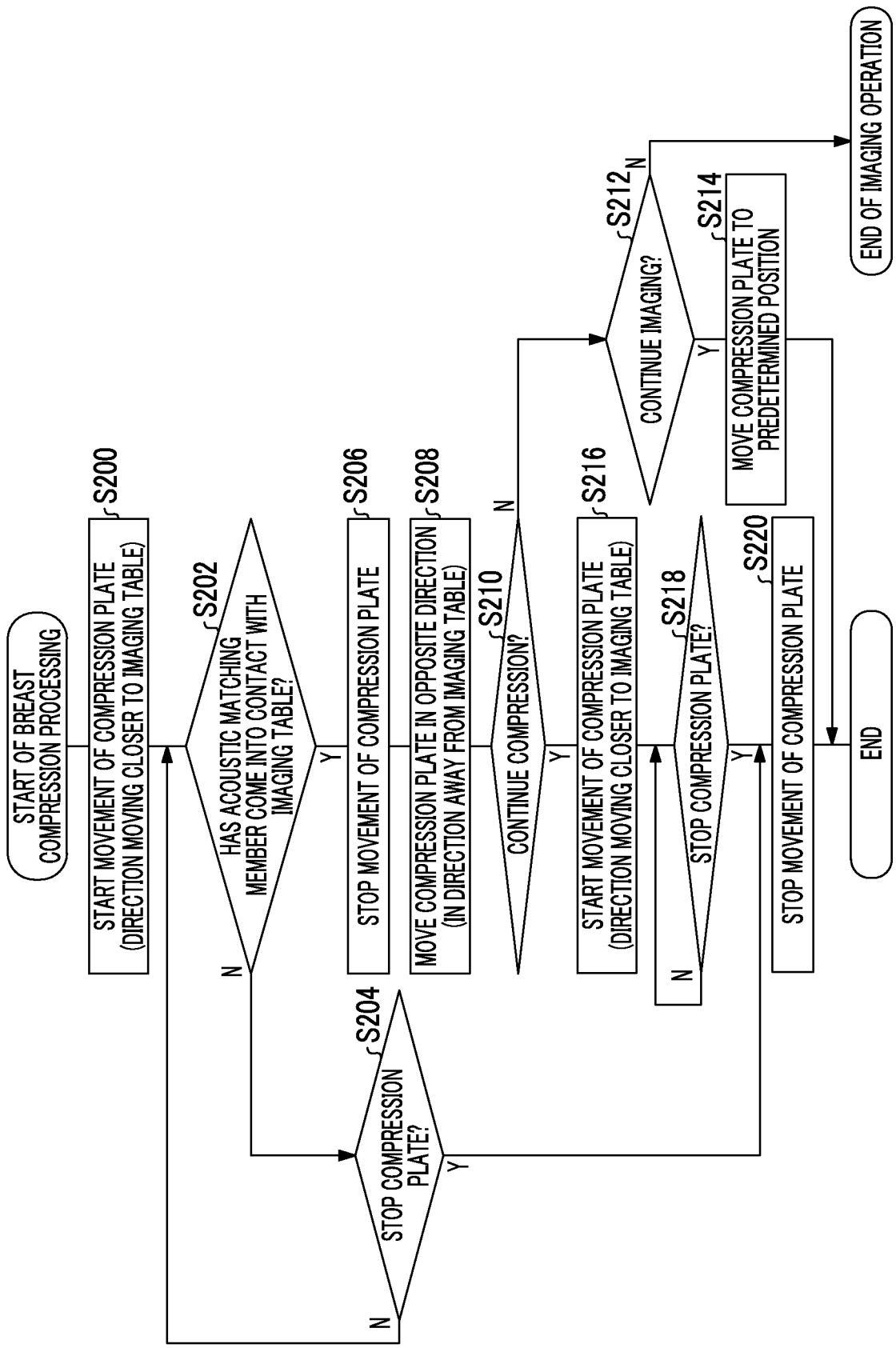

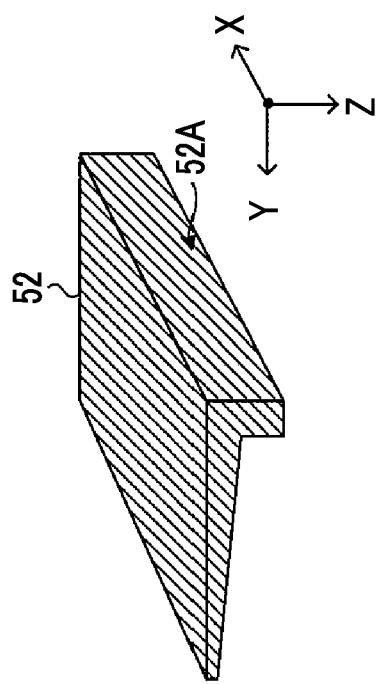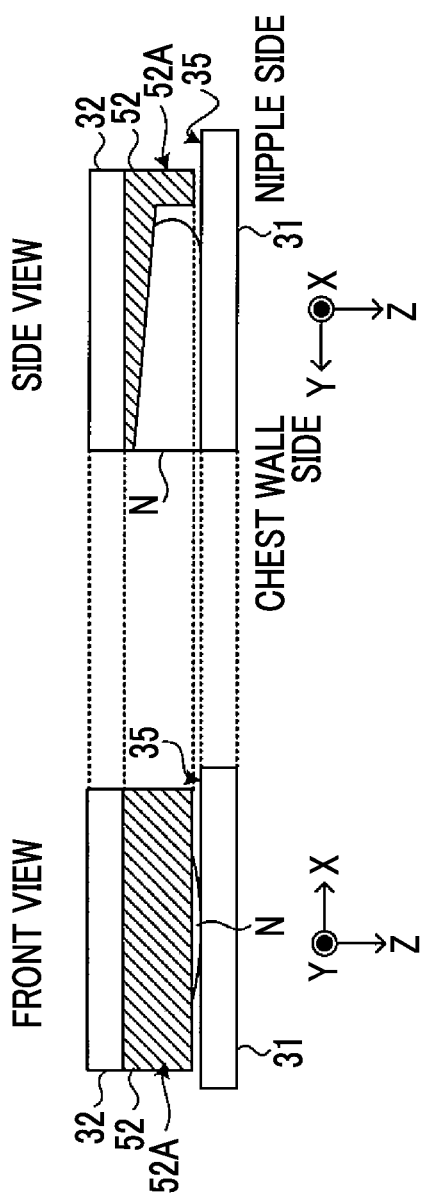

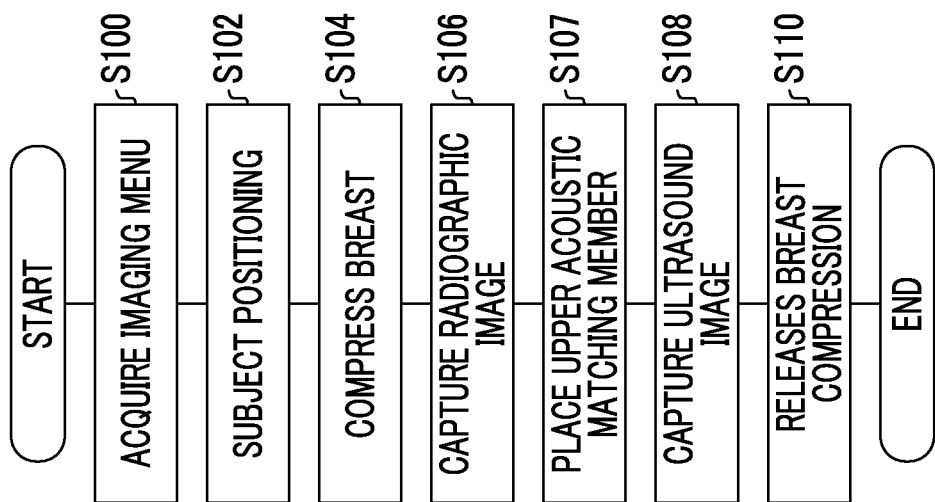

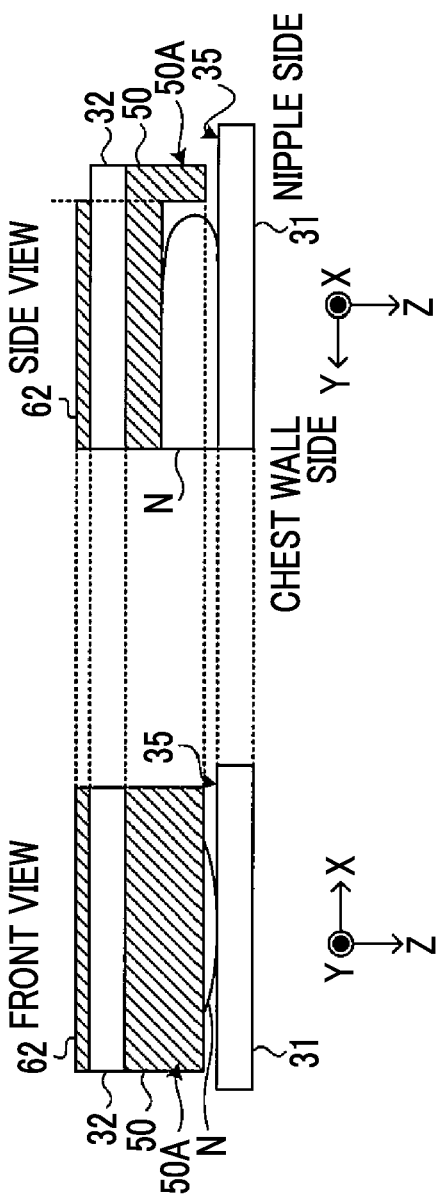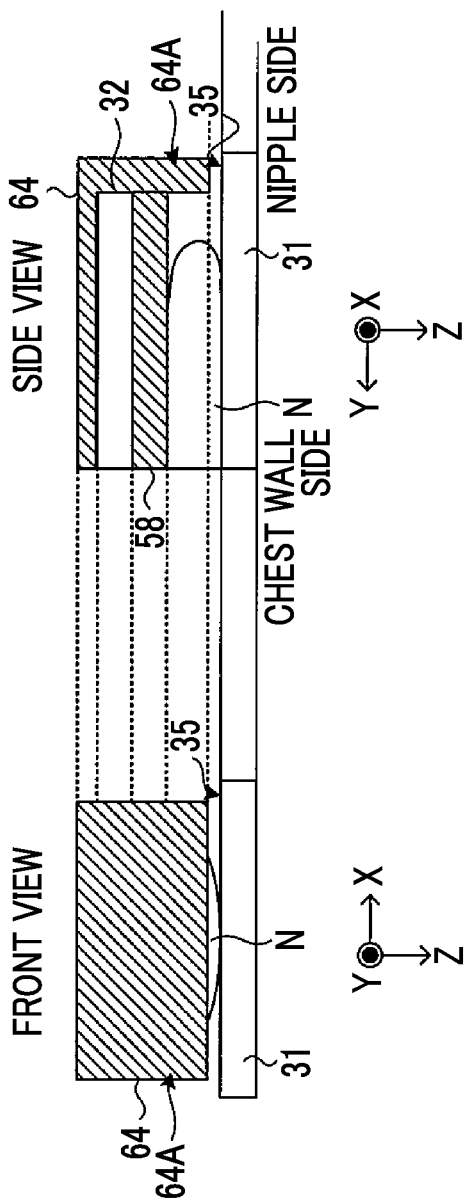

ACOUSTIC MATCHING MEMBER, ACOUSTIC MATCHING MEMBER GROUP, AND MEDICAL IMAGING APPARATUS

CROSS-REFERENCE TO RELATED APPLICATION

This application claims priority from Japanese Patent Application No. 2016-074328, filed on Apr. 1, 2016, the disclosure of which is incorporated by reference herein in its entirety.

BACKGROUND

Field of the Invention

The present invention relates to an acoustic matching member, an acoustic matching member group, and a medical imaging apparatus.

Related Art

An ultrasound imaging apparatus is known which captures an ultrasound image of a breast by scanning the breast with ultrasound waves in order to use the ultrasound image for observation and diagnosis of the breast tissue of a subject. As such an ultrasound imaging apparatus, an ultrasound imaging apparatus that captures an ultrasound image in a state in which a breast is compressed by a compression plate is known. In this ultrasound imaging apparatus, since the breast is compressed by the compression plate, the subject feels uncomfortable.

Generally, in the case of capturing an ultrasound image, an acoustic matching member is provided between an ultrasound probe and a breast in order to reduce acoustic impedance mismatch. Therefore, there is a technique for reducing the burden on a subject using an acoustic matching member. For example, JP2005-270677A discloses a technique for reducing the discomfort of a subject by making the compression pressure, with which the breast is compressed, be distributed using an acoustic matching member.

However, since the technique disclosed in JP2005-270677A is for making the compression pressure, with which the breast is compressed, be distributed using an acoustic matching member, there is room for improvement in order to reduce the burden on the subject.

SUMMARY

The invention has been made in view of the above situation, and it is an object of the invention to provide an acoustic matching member, an acoustic matching member group, and a medical imaging apparatus capable of reducing a burden on a subject in the case of imaging the breast of the subject with ultrasound waves in a state in which the breast is compressed by a compression plate.

In order to achieve the aforementioned object, an acoustic matching member of the invention is an acoustic matching member located between a breast and a compression plate. A protruding portion that protrudes toward an imaging table disposed opposite to a compression plate is provided in an end portion on a deepest side when viewed from a chest wall side of a subject in a case of compressing a breast of the subject in contact with the compression plate.

A thickness of the acoustic matching member of the invention on the chest wall side of the subject may be smaller than that in the end portion on the deepest side.

A surface of the acoustic matching member of the invention that is in contact with the breast of the subject may have a recessed shape that is recessed toward a central portion from an end portion in a horizontal direction of the subject.

The acoustic matching member of the invention may have a protruding shape that protrudes toward the imaging table.

The acoustic matching member of the invention may have a higher hardness than a hardness set in advance as a hardness of the breast.

In order to achieve the aforementioned object, an acoustic matching member group of the invention comprises: the acoustic matching member of the invention; and an upper acoustic matching member provided on a surface of the compression plate opposite to a surface facing the imaging table in a case of compressing the breast of the subject in contact with the compression plate.

A static friction coefficient of the acoustic matching member of the acoustic matching member group of the invention may be larger than a static friction coefficient of the upper acoustic matching member.

A thickness of the acoustic matching member of the acoustic matching member group of the invention in a compression direction of the compression plate may be larger than a thickness of the upper acoustic matching member.

The upper acoustic matching member of the acoustic matching member group of the invention may be provided in a region of the compression plate other than a region corresponding to the protruding portion.

In order to achieve the aforementioned object, a medical imaging apparatus of the invention comprises: the acoustic matching member of the invention; an imaging table on which the breast of the subject is placed; a compression plate that compresses the breast in contact with the acoustic matching member; and an ultrasound imaging unit that captures an ultrasound image of the breast.

The medical imaging apparatus of the invention may further comprise: a contact sensor that detects contact of the protruding portion of the acoustic matching member with the imaging table; and a control unit that performs control to reduce a compression pressure of the breast by the compression plate in a case where the contact sensor detects contact of the protruding portion while the compression plate is compressing the breast.

In order to achieve the aforementioned object, a medical imaging apparatus of the invention comprises: the acoustic matching member group of the invention; an imaging table on which the breast of the subject is placed; a compression plate that compresses the breast in contact with the acoustic matching member group; and an ultrasound imaging unit that captures an ultrasound image of the breast.

The medical imaging apparatus of the invention may further comprise a radiographic imaging unit that captures a radiographic image of the breast.

In the invention, it is possible to provide a medical imaging apparatus, an imaging control method, and an imaging control program capable of reducing the burden on the subject in the case of imaging the breast of the subject with ultrasound waves in a state in which the breast is compressed by the compression plate.

BRIEF DESCRIPTION OF THE DRAWINGS

FIG. 3 is a perspective view of an acoustic matching member of Example 1-1 in the first embodiment.

FIG. 4 is a front view when a state, in which a compression plate compresses a breast with the acoustic matching member shown in FIG. 3 interposed between the compression plate and the breast, is viewed from the direction of the nipple of the breast and a side view when the state is viewed from the side surface of the subject.

FIG. 6 is a flowchart showing the breast compression processing flow of the medical imaging apparatus of the first embodiment.

FIG. 7 is a perspective view of an acoustic matching member of Example 1-2 in the first embodiment.

FIG. 8 is a front view when a state, in which a compression plate compresses a breast with the acoustic matching member shown in FIG. 7 interposed between the compression plate and the breast, is viewed from the direction of the nipple of the breast and a side view when the state is viewed from the side surface of the subject.

FIG. 14 is a flowchart showing an imaging operation in a continuous imaging mode in which a medical imaging apparatus of the second embodiment continuously captures a radiographic image and an ultrasound image.

FIG. 15 is a front view when a state, in which a compression plate compresses a breast with an acoustic matching member of Example 2-2 in the second embodiment interposed between the compression plate and the breast, is viewed from the direction of the nipple of the breast and a side view when the state is viewed from the side surface of the subject.

FIG. 16 is a front view when a state, in which a compression plate compresses a breast with an acoustic matching member interposed between the compression plate and the breast in a case where an upper acoustic matching member in the second embodiment has a protruding portion protruding toward an imaging table, is viewed from the direction of the nipple of the breast and a side view when the state is viewed from the side surface of the subject.

DETAILED DESCRIPTION

Hereinafter, embodiments of the invention will be described in detail with reference to the diagrams. In addition, these embodiments do not limit the invention.

First Embodiment

Example 1-1

First, the configuration of a medical imaging apparatus according to the present embodiment will be described with reference to FIG. 1.

A medical imaging apparatus 10 of the present embodiment has a function of a radiation mammography apparatus, which captures a radiographic image by emitting a radiation R to the breast of a subject and detecting the radiation R transmitted through the breast, and a function of an ultrasound imaging apparatus, which captures an ultrasound image by transmitting an ultrasound wave to the breast of the subject and receiving an ultrasound echo reflected from the inside of the breast. Hereinafter, the capturing of a radiographic image and the capturing of an ultrasound image are simply referred to as "capturing" in a case where these are collectively described without distinction.

Figure 1:
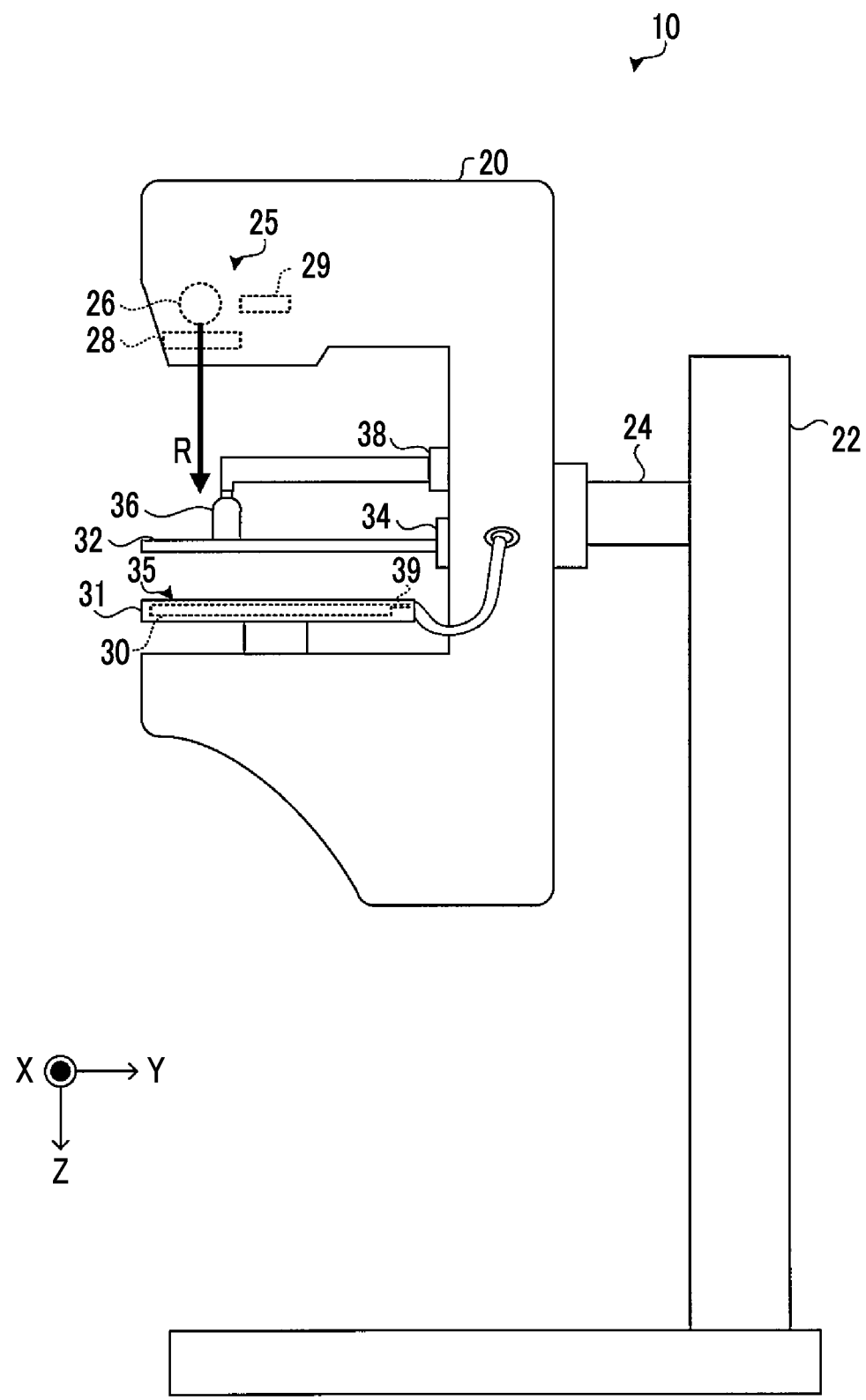
FIG. 1 is a side view showing the appearance of an imaging unit of a medical imaging apparatus of a first embodiment.

As shown in FIG. 1, the medical imaging apparatus 10 of the present embodiment includes an arm unit 20, a base 22, and a shaft unit 24. The base 22 holds the arm unit 20 so as to be movable in a vertical direction (Z-axis direction). The shaft unit 24 connects the arm unit 20 to the base 22. The arm unit 20 can rotate relatively with respect to the base 22 with the shaft unit 24 as a rotary axis.

A radiation emitting section 25, an imaging table 31, a compression plate 32, a compression plate moving mechanism 34, an ultrasound probe 36, and a probe moving mechanism 38 are provided in the arm unit 20.

The radiation emitting section 25 includes a radiation tube 26, a filter 28, and a high voltage generating section 29. The radiation tube 26 generates the radiation R when a tube voltage is applied. The filter 28 is formed of a material, such as molybdenum (Mo) or rhodium (Rh), so that a desired wavelength component among a plurality of wavelength components included in the radiation R generated by the radiation tube 26 is selectively transmitted therethrough.

In the case of performing imaging, the breast of a subject is positioned on an imaging surface 35 of the imaging table 31. The imaging table 31 or the like with which the breast of the subject is in contact is formed of, for example, carbon from the viewpoint of the transparency or intensity of the radiation R. A radiation detector 30 for detecting the radiation R transmitted through the breast and the imaging table 31 is disposed inside the imaging table 31. A radiographic image is generated based on the radiation R detected by the radiation detector 30. The type of the radiation detector 30 of the present embodiment is not particularly limited, and may be an indirect conversion type radiation detector that converts the radiation R into light and converts the converted light into electric charges or may be a direct conversion type radiation detector that converts the radiation R directly into electric charges, for example.

A contact sensor 39 for detecting the contact of an object with respect to the imaging table 31 is disposed inside the imaging table 31. Specifically, the contact sensor 39 of the present embodiment detects whether or not a protruding portion 50A (refer to FIGS. 3 and 4) of an acoustic matching member 50 has come into contact with the imaging table 31. As a specific example of the contact sensor 39, a pressure sensor for detecting the pressure that is applied to the imaging table 31 by the contact of the acoustic matching member 50 can be mentioned, but the contact sensor 39 is not limited thereto.

The compression plate 32 is moved in the vertical direction (Z-axis direction) by the compression plate moving mechanism 34, so that the breast of the subject is compressed between the compression plate 32 and the imaging table 31. It is preferable that the compression plate 32 is optically transparent in order to check positioning or the compression state in compression of the breast, and is formed of a material excellent in transparency with respect to the radiation R so that the radiation R emitted from the radiation emitting section 25 is easily transmitted therethrough. In addition, it is preferable that the compression plate 32 is formed of a material through which ultrasound waves transmitted from the ultrasound probe 36 easily propagate. As a material of the compression plate 32, for example, a resin such as polymethylpentene, polycarbonate, acrylic, and polyethylene terephthalate can be used. In particular, polymethylpentene has low stiffness and excellent stretchability and flexibility and has suitable physical property values in terms of acoustic impedance affecting the reflectance of ultrasound waves and an attenuation coefficient affecting the attenuation of ultrasound waves. Therefore, polymethylpentene has is suitable as a material of the compression plate 32.

The ultrasound probe 36 is moved along the upper surface (surface opposite to a surface in contact with the breast of the subject) of the compression plate 32 by the probe moving mechanism 38, and scans the breast with ultrasound waves to acquire an ultrasound image of the breast. The ultrasound probe 36 includes a plurality of ultrasound transducers (not shown) arranged in a one-dimensional manner or in a two-dimensional manner. Each of the ultrasound transducers transmits ultrasound waves based on the applied driving signal and receives the ultrasound echo to output the reception signal.

Each of the plurality of ultrasound transducers is configured by a transducer in which electrodes are formed at both ends of a piezoelectric material (piezoelectric body), such as piezoelectric ceramic represented by lead (Pb) zirconate titanate (PZT) and a polymer piezoelectric element represented by polyvinylidene difluoride (PVDF), for example. When a pulsed or continuous-wave driving signal is transmitted to the electrodes of the transducer to apply a voltage, the piezoelectric body expands and contracts. Due to the expansion and contraction, pulsed or continuous-wave ultrasound waves are generated from each transducer, and these ultrasound waves are combined to form an ultrasound beam. Each transducer expands and contracts by receiving propagating ultrasound waves, thereby generating an electric signal. The electric signal is output from the transducer as a reception signal of ultrasound waves, and is input to a control unit 40 (refer to FIG. 2) through a cable (not shown).

In the medical imaging apparatus 10 of the present embodiment, in the case of performing ultrasound imaging, the control unit 40 (refer to FIG. 2) moves the ultrasound probe 36 using the probe moving mechanism 38 so that an ultrasound image is automatically captured without the operator moving the ultrasound probe 36. Without being limited to the present embodiment, the operator may move the ultrasound probe 36 to capture an ultrasound image.

Figure 2:
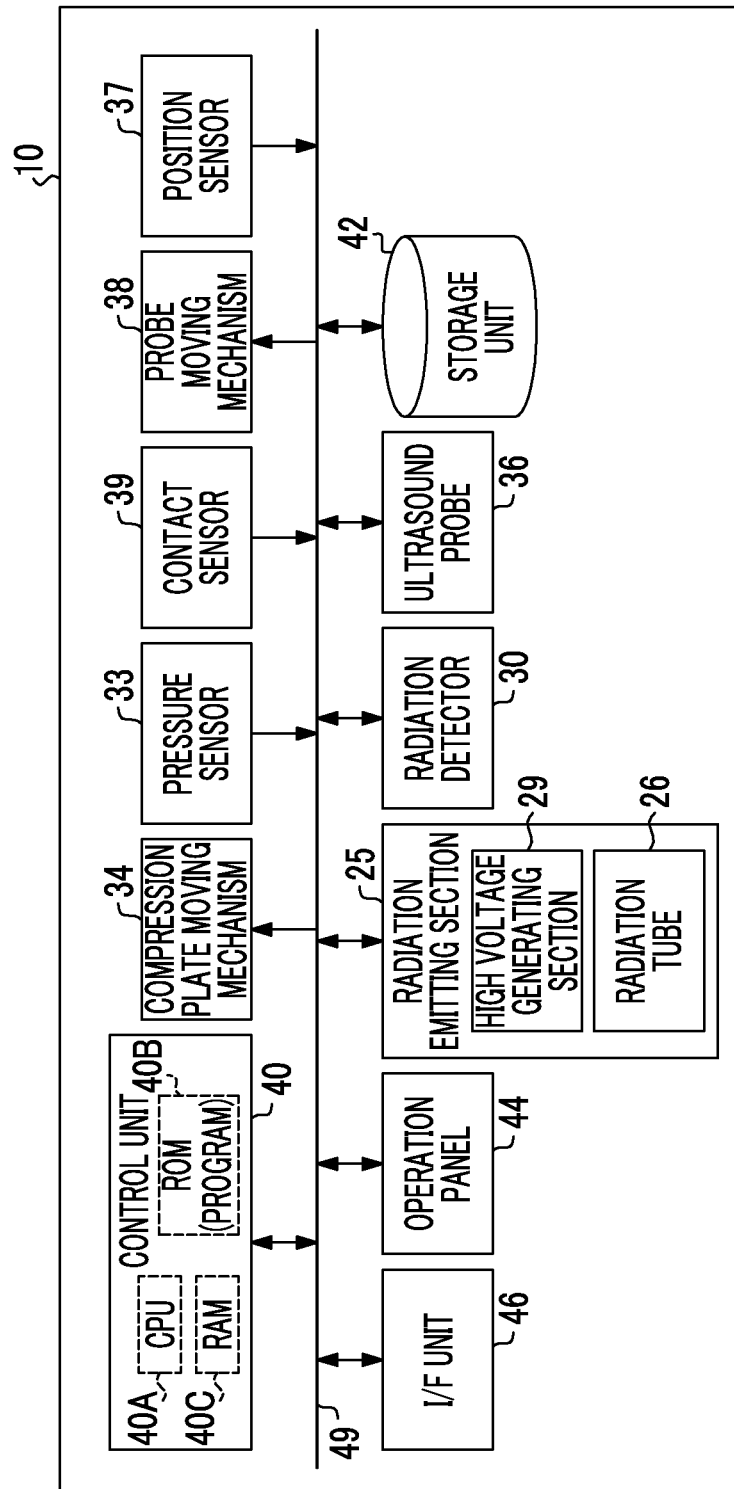
FIG. 2 is a block diagram showing the configuration of the medical imaging apparatus of the first embodiment.

As shown in FIG. 2, the medical imaging apparatus 10 of the present embodiment includes a pressure sensor 33, a position sensor 37, the control unit 40, a storage unit 42, an operation panel 44, and an interface (I/F) unit 46. The radiation emitting section 25, the radiation detector 30, the pressure sensor 33, the compression plate moving mechanism 34, the ultrasound probe 36, the position sensor 37, the probe moving mechanism 38, the control unit 40, the storage unit 42, the operation panel 44, and the interface (I/F) unit 46 are connected to each other so that transmission and reception of various signals therebetween are possible through a bus 49, such as a system bus or a control bus.

The control unit 40 includes a central processing unit (CPU) 40A, a read only memory (ROM) 40B, and a random access memory (RAM) 40C. Various programs executed by the CPU 40A are stored in advance in the ROM 40B. The RAM 40C stores various kinds of data temporarily.

The pressure sensor 33 detects the compression pressure by the compression plate 32. The position sensor 37 is built into the ultrasound probe 36, and detects the position (position on the surface of compression plate 32) of the ultrasound probe 36.

The control unit 40 controls the overall operation of the medical imaging apparatus 10. In the case of capturing a radiographic image, the control unit 40 of the present embodiment controls the radiation emitting section 25, the radiation detector 30, and the compression plate moving mechanism 34. Based on the detection result of the pressure sensor 33, the control unit 40 moves the compression plate 32 using the compression plate moving mechanism 34 so that the breast is compressed between the compression plate 32 and the imaging table 31. The control unit 40 applies a high voltage generated by the high voltage generating section 29 to the radiation tube 26 by adjusting the imaging conditions, such as a tube voltage or a tube current, so that the radiation R is emitted from the radiation emitting section 25. The control unit 40 causes the radiation detector 30 to detect the radiation R transmitted through the breast, thereby capturing a radiographic image.

In the case of capturing an ultrasound image, the control unit 40 of the present embodiment controls the ultrasound probe 36 and the probe moving mechanism 38. The control unit 40 checks the position of the ultrasound probe 36 based on the detection result of the position sensor 37, and moves the ultrasound probe 36 using the probe moving mechanism 38. The control unit 40 captures an ultrasound image by transmitting and receiving ultrasound waves while moving the ultrasound probe 36 using the probe moving mechanism 38.

Image data, other various kinds of information, and the like of radiographic images and ultrasound images obtained by imaging are stored in the storage unit 42. As specific examples of the storage unit 42, a hard disk drive (HDD), a solid state drive (SSD), and the like can be mentioned.

The operation panel 44 receives an instruction (for example, an instruction to compress the breast with the compression plate 32) regarding imaging by the operator. The operation panel 44 is provided in the arm unit 20 of the medical imaging apparatus 10, for example. In addition, the operation panel 44 may be provided as a touch panel in which a display unit and an input unit are combined.

The I/F unit 46 communicates various kinds of information with an external device (not shown), such as a console, or an external system (for example, a radiology information system (RIS; not shown)), by wireless communications or cable communication. in the medical imaging apparatus 10 of the present embodiment, the captured radiographic image or ultrasound image is transmitted from the I/F unit 46 to an external device, such as a console, or an external device, such as an image interpretation device.

Next, capturing of a radiographic image and an ultrasound image in the medical imaging apparatus 10 of the present embodiment will be described.

The medical imaging apparatus 10 of the present embodiment has an imaging mode for continuously capturing a radiographic image and an ultrasound image (hereinafter, referred to as a "continuous imaging mode") and an imaging mode for capturing one of a radiographic image and an ultrasound image. Hereinafter, a case where the medical imaging apparatus 10 executes the continuous imaging mode will be described.

In the medical imaging apparatus 10 of the present embodiment, in the case of capturing an ultrasound image of a breast in a state in which the breast is compressed by the compression plate 32, the acoustic matching member 50 whose example is shown in FIGS. 3 and 4 is provided between the compression plate 32 and the breast in order to reduce the acoustic impedance mismatch at the contact surface between the compression plate 32 and the breast. FIG. 3 shows a perspective view of the acoustic matching member 50, and FIG. 4 shows a front view when a state, in which the compression plate 32 compresses the breast N with the acoustic matching member 50 interposed between the compression plate 32 and the breast N, is viewed from the direction of the nipple of the breast N and a side view when the state is viewed from the side surface of the subject.

As shown in FIGS. 3 and 4, in the acoustic matching member 50 of the present embodiment, the protruding portion 50A that protrudes toward the imaging table 31 is provided in an end portion on the nipple side of the subject (end portion on the deepest side when viewed from the chest wall of the subject). As shown in FIG. 4, in the space formed by the acoustic matching member 50 and the imaging table 31, the breast N is compressed by the compression plate 32. In the acoustic matching member 50 of the present embodiment, the protruding portion 50A is not in contact with the imaging table 31 in a state in which the breast N is compressed. Therefore, the length of the protruding portion 50A that protrudes toward the imaging table 31 is determined based on the thickness (thickness in the Z-axis direction) when the general breast N is compressed in capturing of a radiographic image and an ultrasound image.

On the other hand, the thickness of a portion of the acoustic matching member 50 in contact with the breast N is the same on the entire rectangular surface in contact with the compression plate 32, and the specific thickness may be determined, for example, from the viewpoint of matching the acoustic impedance. The length of each side of the acoustic matching member 50 on the rectangular surface in contact with the compression plate 32 is the same as the length of each side of the compression plate 32 on a surface in contact with the acoustic matching member 50. By the setting of such a length, in a case where the operator performs positioning of the acoustic matching member 50, it is sufficient to match the shape of the compression plate 32. Accordingly, the positioning becomes easy. In the present embodiment, "same" refers to a range that can be regarded as the same, including an error or an allowable range.

In the present embodiment, the acoustic matching member 50 is formed of a material having both good compatibility with a living body (breast N in the present embodiment) and good transparency of ultrasound waves. It is preferable that the acoustic matching member 50 is formed of a material that is flexible, has physical strength and good transparency of ultrasound waves, and can withstand sterilization treatment. As materials of the acoustic matching member 50, a non-hydrogel material, a polymeric hydrogel, and the like are used. As specific materials of the acoustic matching member 50, carboxyvinyl polymer, glycerin, polyvinyl pyrrolidone (PVP), polyurethane, polyvinyl alcohol (PVA) based polymer gel, urethane rubber, silicone rubber, polyethylene oxide (PEO), and the like are used. The surface of the acoustic matching member 50 of the present embodiment may be covered with silicone rubber or the like in order to maintain the shape.

In the present embodiment, it is preferable that the hardness of the acoustic matching member 50 is higher than the hardness of the general breast N (in other words, the acoustic matching member 50 is harder than the general breast N). In addition, it is preferable that the hardness of the acoustic matching member 50 is lower than the hardness of the compression plate 32 (in other words, the acoustic matching member 50 is softer than the compression plate 32). By setting the hardness of the acoustic matching member 50 as described above, the effect of uniformly compressing the breast N in a desired shape is enhanced, and the effect of suppressing excessive compression of the breast N is enhanced.

For the hardness of the acoustic matching member 50, it is preferable that, in the Y-axis direction, the hardness on the chest wall side of the breast N is lower than the hardness on the nipple side (in other words, the acoustic matching member 50 on the chest wall side of the breast N is softer than the acoustic matching member 50 on the nipple side). In this case, since the acoustic matching member 50 tends to be deformed on the chest wall side compared with the nipple side, the acoustic matching member 50 is likely to be deformed according to the shape of the breast N. Therefore, it is possible to reduce the burden on the subject.

A method of placing the acoustic matching member 50 on the upper surface of the breast N is not particularly limited. In a case where the acoustic matching member 50 is attachable to the surface of the compression plate 32 on the breast side, the breast N may be compressed by the compression plate 32 in a state in which the acoustic matching member 50 is attached to the compression plate 32. In addition, the breast N may also be compressed by the compression plate 32 in a state in which the operator has placed the acoustic matching member 50 on the breast N.

In the case of executing the continuous imaging mode in the medical imaging apparatus 10 of the present embodiment, both the capturing of a radiographic image and the capturing of an ultrasound image are continuously performed in a state in which the compression plate 32 compresses the breast until the end of the capturing of a radiographic image and the capturing of an ultrasound image, without releasing the compression of the breast. Therefore, as shown in FIG. 4, capturing of a radiographic image and capturing of an ultrasound image are performed in a state in which the acoustic matching member 50 required in the capturing of an ultrasound image is provided between the compression plate 32 and the breast N.

Figure 5:
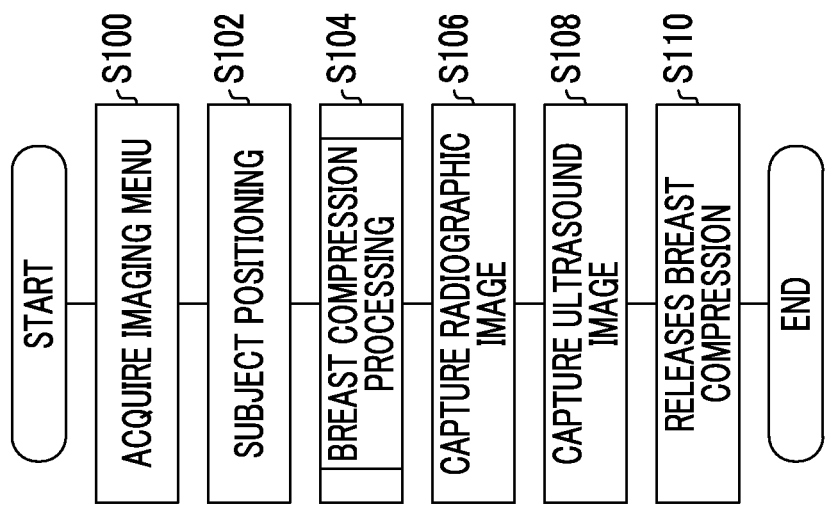
FIG. 5 is a flowchart showing an imaging operation in a continuous imaging mode in which the medical imaging apparatus of the first embodiment continuously captures a radiographic image and an ultrasound image.

FIG. 5 shows the overall flow of a series of imaging operations in a case where the operator captures a radiographic image and an ultrasound image in the continuous imaging mode using the medical imaging apparatus 10 of the present embodiment.

First, the control unit 40 of the medical imaging apparatus 10 acquires an imaging menu in step S100. The imaging menu includes information, such as imaging conditions, a subject, and the breast N. For example, the control unit 40 may acquire an imaging menu from an external device, such as a console, through the I/F unit 46, or may acquire an imaging menu that the operator inputs through the operation panel 44.

In the next step S102, the operator positions the breast N of the subject on the imaging table 31.

Then, in the next step S104, the medical imaging apparatus 10 performs breast compression processing (refer to FIG. 6) for compressing the breast N of the subject with the compression plate 32 in a state in which the acoustic matching member 50 is provided on the upper surface (surface on the compression plate 32 side) of the breast N, which will be described in detail later.

In the next step S106, the medical imaging apparatus 10 captures a radiographic image of the breast N. In the case of capturing a radiographic image, the control unit 40 retracts the ultrasound probe 36 to the outside of the radiographic image detection region of the radiation detector 30 using the probe moving mechanism 38. The image data of the captured radiographic image may be output to an external device, such as a console, immediately after capturing the radiographic image. Alternatively, the image data of the captured radiographic image may be temporarily stored in the storage unit 42, and image data of both images may be output to an external device, such as a console, after the end of the capturing of a radiographic image and an ultrasound image.

After the end of the capturing of the radiographic image, the medical imaging apparatus 10 captures an ultrasound image of the breast N in the next step S108. As described above, the control unit 40 causes the probe moving mechanism 38 to move the ultrasound probe 36 along the surface of the compression plate 32 facing the radiation tube 26 while causing the position sensor 37 to detect the position of the ultrasound probe 36. Then, the control unit 40 captures an ultrasound image by transmitting an ultrasound wave to the breast N from the ultrasound probe 36 and receiving the ultrasound echo reflected from the inside of the breast N.

After the end of the capturing of the ultrasound image, the medical imaging apparatus 10 releases the compression of the breast N by the compression plate 32 in the next step S110. Specifically, the operator inputs an instruction to move the compression plate 32 (instruction to release the compression) through the operation panel 44. The control unit 40 releases the compression of the breast N by moving the compression plate 32 in a direction away from the imaging table 31 using the compression plate moving mechanism 34 in accordance with the instruction input of the operator.

When the compression of the breast N is released in this manner, the imaging operation in the continuous imaging mode ends.

Next, the breast compression processing of the present embodiment executed in above step S104 will be described with reference to FIG. 6. FIG. 6 is a flowchart of an example of the breast compression processing executed by the control unit 40 in step S104.

In the medical imaging apparatus 10 of the present embodiment, when the positioning of the breast N of the subject is completed, the operator inputs a compression instruction to move the compression plate 32 through the operation panel 44. When the compression instruction is received, the control unit 40 executes the breast compression processing shown in FIG. 6.

In step S200, the control unit 40 starts the movement of the compression plate 32. Specifically, the control unit 40 causes the compression plate moving mechanism 34 to move the compression plate 32 in a direction moving closer to the imaging table 31.

In the next step S202, the control unit 40 determines whether or not the acoustic matching member 50 has come into contact with the imaging table 31 based on the detection result of the contact sensor 39. In a case where the acoustic matching member 50 is not in contact with the imaging table 31, negative determination is made, and the process proceeds to step S204.

In step S204, the control unit 40 determines whether or not to stop the compression plate 32. In the medical imaging apparatus 10 of the present embodiment, in the case of performing imaging, a desired compression pressure for compressing the breast N is determined in advance in the apparatus. Therefore, in this step, the control unit 40 determines whether or not to stop the compression plate 32 according to whether or not the compression pressure detected by the pressure sensor 33 has reached a desired compression pressure. In a case where the compression pressure detected by the pressure sensor 33 has not reached a desired compression pressure, negative determination is made, and the process returns to step S202. On the other hand, in a case where the compression pressure detected by the pressure sensor 33 has reached a desired compression pressure, positive determination is made, and the process proceeds to step S220.

On the other hand, in a case where the acoustic matching member 50 has come into contact with the imaging table 31 in step S202, positive determination is made, and the process proceeds to step S206.

In step S206, the control unit 40 stops the movement of the compression plate 32. Then, in the next step S208, the control unit 40 starts the movement of the compression plate 32 in the opposite direction. Specifically, the control unit 40 causes the compression plate moving mechanism 34 to move the compression plate 32 in a direction away from the imaging table 31. In this step, the distance by which the control unit 40 moves the compression plate 32 is not particularly limited, and the compression plate 32 may be moved to a position where compression against the breast N is completely released, or the compression plate 32 may be moved by a predetermined distance regardless of whether or not compression is completely released.

In the next step S210, the control unit 40 determines whether or not to continue compressing the breast N. In the present embodiment, as described above, in a case where the acoustic matching member 50 has come into contact with the imaging table 31, there is a concern that the breast N is excessively compressed regardless of the compression pressure. Accordingly, the control unit 40 stops the movement of the compression plate 32 in step S206 and moves the compression plate 32 in a direction away from the imaging table 31 in step S208, thereby reducing the burden (compression) on the subject. However, depending on the shape, state, or the like of the breast N of the subject, even in a case where the acoustic matching member 50 has come into contact with the imaging table 31, the burden on the subject that is applied by compressing the compression plate 32 may not be large, and it may be necessary to further compress the breast N. In such a case, in the medical imaging apparatus 10 of the present embodiment, it is possible to continue compressing the breast N even after the acoustic matching member 50 has come into contact with the imaging table 31. In such a case, therefore, the operator inputs an instruction to continue compressing the compression plate 32 through the operation panel 44.

In a case where no compression continuation instruction is received even after the passage of a predetermined amount of time, negative determination is made in step S210, and the process proceeds to step S212. In step S212, the control unit 40 determines whether or not to continue imaging. Before the compression pressure for compressing the breast N reaches a desired compression pressure, the acoustic matching member 50 comes into contact with the imaging table 31. Accordingly, in a case where compression is not continued, even if the breast N is compressed again by the compression plate 32, there is a high possibility that the acoustic matching member 50 will come into contact with the imaging table 31 before the compression pressure for compressing the breast N reaches the desired compression pressure. However, even in a state in which the compression pressure for compressing the breast N does not reach the desired compression pressure, the operator may desire to continue imaging. In such a case, the operator inputs an instruction to continue the imaging through the operation panel 44.

In a case where no imaging continuation instruction is received even after the passage of a predetermined amount of time, negative determination is made in step S212, and this breast compression processing is ended. At the same time, the imaging operation itself shown in FIG. 5 is ended.

On the other hand, in a case where an imaging continuation instruction is received, positive determination is made in step S212, and the process proceeds to step S214. In step S214, the control unit 40 moves the compression plate 32 to a predetermined position in a direction moving closer to the imaging table 31, and ends this breast compression processing. The predetermined position is not particularly limited. For example, a position where the distance between the acoustic matching member 50 and the imaging table 31 takes a value considering the size of the general breast N or the like may be set in the apparatus in advance as the predetermined position. Without being limited to this, the control unit 40 may stop the movement of the compression plate 32 in response to a stop instruction to stop the movement of the compression plate 32 that has been input through the operation panel 44 by the operator.

On the other hand, in a case where a compression continuation instruction is received in the above step S210, positive determination is made, and the process proceeds to step S216. In step S216, the control unit 40 starts the movement of the compression plate 32 in a direction moving closer to the imaging table 31.

In the next step S218, the control unit 40 determines whether or not to stop the compression plate 32. In this step, the control unit 40 stops the movement of the compression plate 32 in at least one of a case where the compression pressure detected by the pressure sensor 33 reaches a desired compression pressure or a case where a stop instruction is received. In a case where the movement of the compression plate 32 is not to be stopped, negative determination is made to enter a standby state. On the other hand, in a case where the movement of the compression plate 32 is to be stopped, positive determination is made, and the process proceeds to step S220.

In step S220, the control unit 40 stops the movement of the compression plate 32, and then ends this breast compression processing.

The shape of the acoustic matching member 50 in the present embodiment is not limited to the shape shown in FIGS. 3 and 4, and may be a shape in which the protruding portion 50A that protrudes toward the imaging table 31 is provided in an end portion on the nipple side of the subject (end portion on the deepest side when viewed from the chest wall of the subject). The shape of the acoustic matching member shown in FIGS. 3 and 4 is assumed to be Example 1-1, and other shapes of the acoustic matching member of the present embodiment will be described in the following examples.

Example 1-2

FIG. 7 shows a perspective view of an acoustic matching member 52 of this example, and FIG. 8 shows a front view when a state, in which the compression plate 32 compresses the breast N with the acoustic matching member 52 interposed between the compression plate 32 and the breast N, is viewed from the direction of the nipple of the breast N and a side view when the state is viewed from the side surface of the subject.

As shown in FIGS. 7 and 8, the acoustic matching member 52 of this example has a protruding portion 52A in the same manner as the acoustic matching member 50 (refer to FIGS. 3 and 4) of the example described above, but the thickness of a portion in contact with the breast N changes along the Y-axis direction.

As shown in FIGS. 7 and 8, in the acoustic matching member 52 of this example, the thickness of a portion in contact with the breast N is the smallest on the chest wall side and the largest on the nipple side.

In general, the thickness of the breast N in the vertical direction of the subject increases toward the chest wall side and decreases toward the nipple side. Therefore, by forming the acoustic matching member 52 in the shape shown in FIGS. 7 and 8, it is possible to perform compression according to the shape of the breast N. As a result, it is possible to reduce the compression pressure applied to the chest wall side. Thus, according to the acoustic matching member 52 of this example, it is possible to reduce the burden on the subject at the time of compression using the compression plate 32.

Example 1-3

Figure 9:
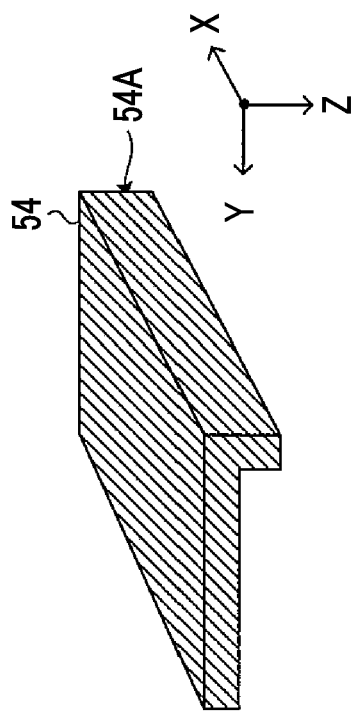
FIG. 9 is a perspective view of an acoustic matching member of Example 1-3 in the first embodiment.
Figure 10:
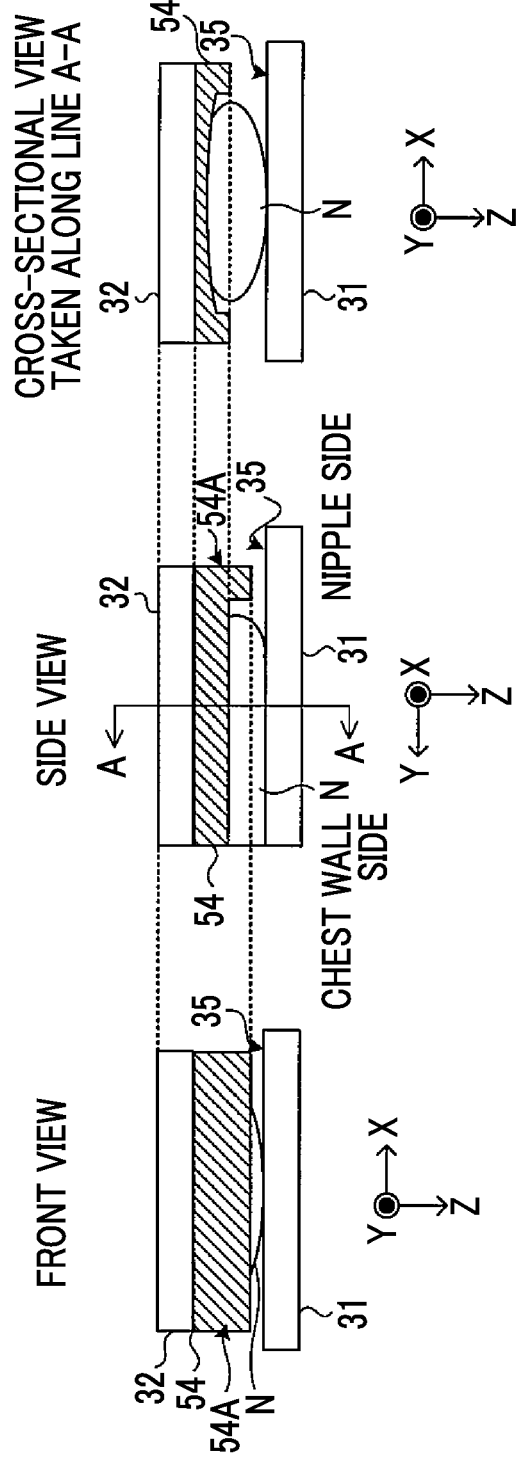
FIG. 10 is a front view when a state, in which a compression plate compresses a breast with the acoustic matching member shown in FIG. 9 interposed between the compression plate and the breast, is viewed from the direction of the nipple of the breast, a side view when the state is viewed from the side surface of the subject, and a cross-sectional view taken along the line A-A in the side view.

FIG. 9 shows a perspective view of an acoustic matching member 54 of this example, and FIG. 10 shows a front view when a state, in which the compression plate 32 compresses the breast N with the acoustic matching member 54 interposed between the compression plate 32 and the breast N, is viewed from the direction of the nipple of the breast N, a side view when the state is viewed from the side surface of the subject, and a cross-sectional view taken along the line A-A in the side view.

As shown in FIGS. 9 and 10, the acoustic matching member 54 of this example has a protruding portion 54A in the same manner as the acoustic matching member 50 (refer to FIGS. 3 and 4) of the example described above, but the thickness of a portion in contact with the breast N changes along the X-axis direction.

As shown in FIGS. 9 and 10, in the acoustic matching member 54 of this example, the shape of a portion in contact with the breast N is a recessed shape that is recessed toward the central portion from the end portion in the horizontal direction of the subject.

In general, the thickness of the breast N in the horizontal direction (corresponding to the X-axis direction in the diagram) of the subject increases toward the central portion and decreases toward the end portion. Therefore, by forming the acoustic matching member 54 in the shape shown in FIGS. 9 and 10, it is possible to perform compression according to the shape of the breast N. As a result, it is possible to reduce the compression pressure applied to the chest wall side. Thus, according to the acoustic matching member 54 of this example, it is possible to reduce the burden on the subject at the time of compression using the compression plate 32.

Example 1-4

Figure 11:
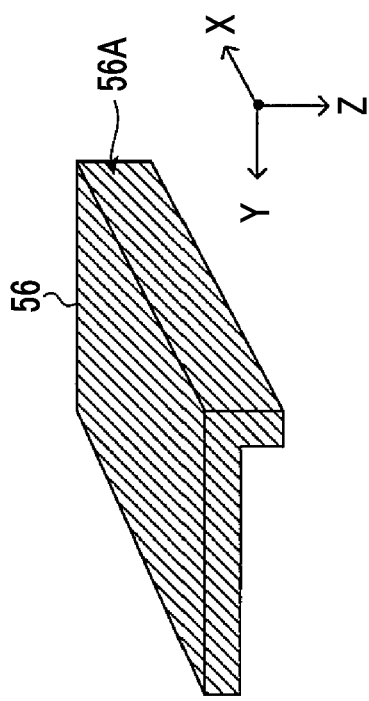
FIG. 11 is a perspective view of an acoustic matching member of Example 1-4 in the first embodiment.
Figure 12:
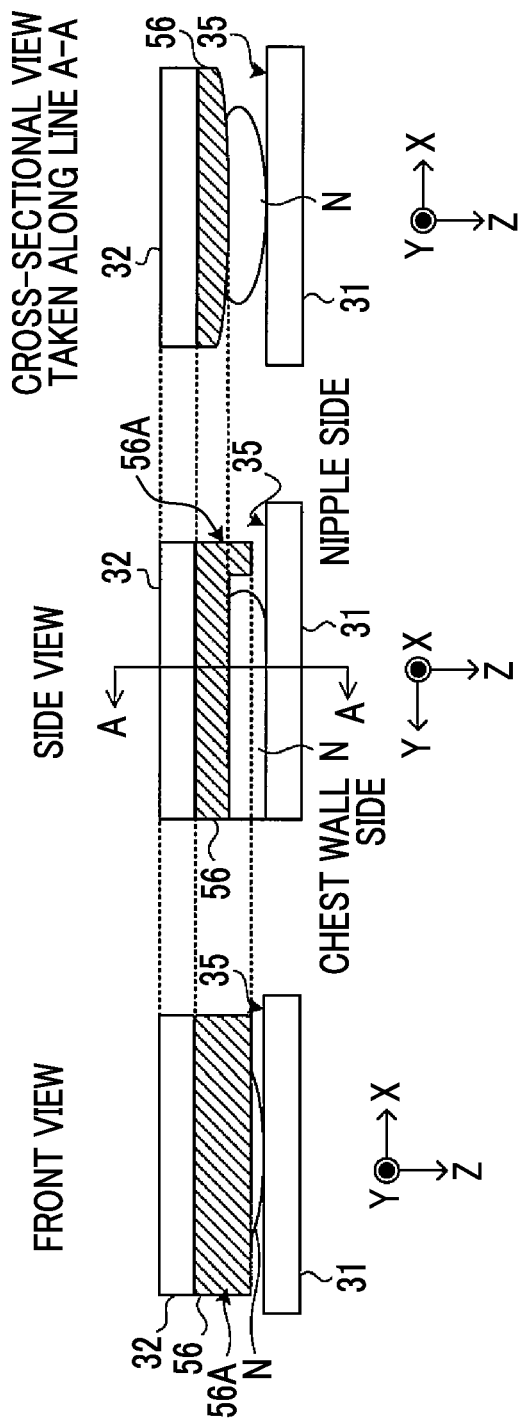
FIG. 12 is a front view when a state, in which a compression plate compresses a breast with the acoustic matching member shown in FIG. 11 interposed between the compression plate and the breast, is viewed from the direction of the nipple of the breast, a side view when the state is viewed from the side surface of the subject, and a cross-sectional view taken along the line A-A in the side view.

FIG. 11 shows a perspective view of an acoustic matching member 56 of this example, and FIG. 12 shows a front view when a state, in which the compression plate 32 compresses the breast N with the acoustic matching member 56 interposed between the compression plate 32 and the breast N, is viewed from the direction of the nipple of the breast N, a side view when the state is viewed from the side surface of the subject, and a cross-sectional view taken along the line A-A in the side view.

As shown in FIGS. 11 and 12, the acoustic matching member 56 of this example has a protruding portion 56A in the same manner as the acoustic matching member 50 (refer to FIGS. 3 and 4) of the example described above, but the thickness of a portion in contact with the breast N changes along the X-axis direction.

As shown in FIGS. 11 and 12, in the acoustic matching member 56 of this example, the shape of a portion in contact with the breast N is a protruding shape that protrudes toward the imaging table 31. Specifically, the thickness of a portion of the acoustic matching member 56 in contact with the breast N is the largest in a central portion of the compression plate 32 in the X-axis direction, and is the smallest in an end portion of the compression plate 32 in the X-axis direction.

In general, the thickness of the breast N in the horizontal direction of the subject increases toward the central portion and decreases toward the end portion. Therefore, in order to make the thickness of the breast N uniform in the case of compressing the breast N with the compression plate 32, it is preferable to compress the central portion more than the end portion in the horizontal direction of the subject. By forming the acoustic matching member 54 in the shape shown in FIGS. 11 and 12, it is possible to increase the compression pressure toward the central portion in the horizontal direction of the breast N. As a result, it becomes easy to make the thickness of the breast N uniform.

Second Embodiment

Example 2-1

Next, a second embodiment will be described. The same portions as in the medical imaging apparatus 10 and the acoustic matching member of the first embodiment are denoted by the same reference numerals, and the detailed explanation thereof will be omitted.

Since the configuration of the medical imaging apparatus 10 is the same as that of the medical imaging apparatus 10 (refer to FIGS. 1 and 2) of the first embodiment, the explanation thereof will be omitted.

In the medical imaging apparatus 10 of the first embodiment described above, in the case of capturing an ultrasound image, one of the acoustic matching members 50 to 56 is provided between the compression plate 32 and the breast N. In contrast, the medical imaging apparatus 10 of the present embodiment, in the case of capturing an ultrasound image, one of the acoustic matching members 50 to 56 is provided between the compression plate 32 and the breast N, and an upper acoustic matching member is provided on the upper surface (surface not facing the imaging table 31) of the compression plate 32. Hereinafter, a case where the acoustic matching member 50 described in the above Example 1-1 is provided between the compression plate 32 and the breast N will be described as a specific example.

Figure 13:
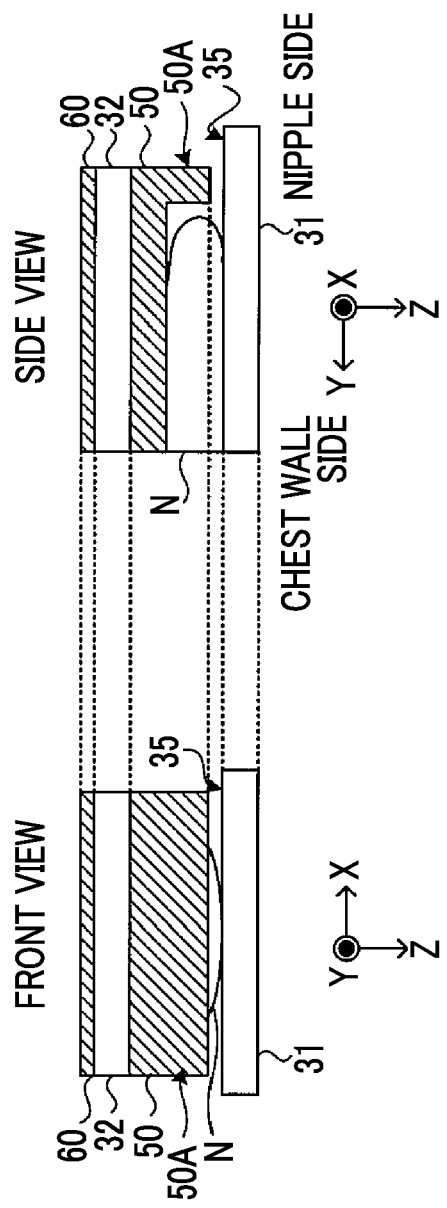
FIG. 13 is a front view when a state, in which a compression plate compresses a breast with an acoustic matching member of Example 2-1 in a second embodiment interposed between the compression plate and the breast, is viewed from the direction of the nipple of the breast and a side view when the state is viewed from the side surface of the subject.

FIG. 13 shows a front view when a state, in which the compression plate 32 compresses the breast N with the acoustic matching member 50 interposed between the compression plate 32 and the breast N, is viewed from the direction of the nipple of the breast N and a side view when the state is viewed from the side surface of the subject.

As shown in FIG. 13, in the present embodiment, the acoustic matching member 50 is provided between the compression plate 32 and the breast N, and an upper acoustic matching member 60 is provided on the upper surface of the compression plate 32. In the case of capturing an ultrasound image, the control unit 40 causes the probe moving mechanism 38 to move the ultrasound probe 36 along the upper surface of the compression plate 32 in a state in which the upper acoustic matching member 60 is provided.

The upper acoustic matching member 60 of the present embodiment has a function as a lubricant in the movement of the ultrasound probe 36 and a function of reducing an acoustic impedance mismatch on the contact surface between the compression plate 32 and the ultrasound probe 36.

The upper acoustic matching member 60 of the present embodiment is a rectangular parallelepiped having the same area as the contact surface of the compression plate 32. As shown in FIG. 13, the thickness of the upper acoustic matching member 60 in the Z-axis direction is smaller than the thickness of the acoustic matching member 50 in the Z-axis direction. As a specific example of the thickness of the acoustic matching member 50 in the Z-axis direction, 1 mm or more can be mentioned.

The acoustic matching member 50 preferably has high adhesion to the breast N, and the upper acoustic matching member 60 preferably has high lubricity in order to move the ultrasound probe 36 smoothly. In the present embodiment, therefore, the static friction coefficient of the acoustic matching member 50 is larger than the static friction coefficient of the upper acoustic matching member 60. As a specific example of the static friction coefficient, 0.2 or more can be mentioned for the acoustic matching member 50, and 0.2 or less can be mentioned for the upper acoustic matching member 60.

In the present embodiment, the upper acoustic matching member 60 is formed of a material having both good lubricity and transparency of ultrasound waves. As the upper acoustic matching member 60 of the present embodiment, a so-called gel pad in which the surface is covered with silicone rubber or the like in order to maintain the shape is used.

As shown in FIG. 14, the overall flow of a series of imaging operations in the case of performing imaging in the continuous imaging mode in the medical imaging apparatus 10 of the present embodiment is different from the overall flow (refer to FIG. 5) of the imaging operation of the first embodiment in that processing in step S107 is performed between steps S106 and S108.

As described above, in the medical imaging apparatus 10 of the present embodiment, in the case of capturing an ultrasound image, the upper acoustic matching member 60 is provided on the upper surface of the compression plate 32. Therefore, as shown in FIG. 14, after the capturing of a radiographic image is ended, the operator places the upper acoustic matching member 60 on the upper surface of the compression plate 32 in step S107.

Although the method of providing the upper acoustic matching member 60 on the upper surface of the compression plate 32 is not particularly limited, it is preferable that the upper acoustic matching member 60 does not move and is in close contact with the compression plate 32 even if the ultrasound probe 36 is moved on the upper surface of the compression plate 32. For example, in a case where the compression plate 32 has a mounting mechanism for mounting the upper acoustic matching member 60 to the upper surface, the upper acoustic matching member 60 may be mounted on the upper surface of the compression plate 32 using the mounting mechanism.

In addition, since breast compression processing executed in the medical imaging apparatus 10 of the present embodiment is the same as the breast compression processing (refer to FIG. 6) executed in the medical imaging apparatus 10 of the first embodiment, the explanation thereof will be omitted.

The shape of the upper acoustic matching member 60 provided on the upper surface of the compression plate 32 in the present embodiment is not limited to the shape shown in FIG. 13, and any shape that covers the region of the compression plate 32 to move the ultrasound probe 36 in the capturing of an ultrasound image may be used. The shape of the upper acoustic matching member shown in FIG. 13 is assumed to be Example 2-1, and other shapes of the upper acoustic matching member of the present embodiment will be described in the following examples.

Example 2-2

FIG. 15 shows a front view when a state, in which the compression plate 32 compresses the breast N with the acoustic matching member 50 interposed between the compression plate 32 and the breast N, is viewed from the direction of the nipple of the breast N and a side view when the state is viewed from the side surface of the subject.

As shown in FIG. 15, an upper acoustic matching member 62 of this example is different from the upper acoustic matching member 60 (refer to FIG. 13) of the example described above in terms of the area (size) of a portion in contact with the compression plate 32.

As shown in FIG. 15, the upper acoustic matching member 62 of this example is not present in a region of the upper surface of the compression plate 32 corresponding to the protruding portion 52A of the acoustic matching member 50.

The breast N is not disposed in the region corresponding to the protruding portion 50A of the acoustic matching member 50. Therefore, in the case of capturing an ultrasound image, scanning by the ultrasound probe 36 is not required for the region of the upper surface of the compression plate 32 corresponding to the protruding portion 52A of the acoustic matching member 50.

Thus, since the upper acoustic matching member 62 is not provided in the region of the upper surface of the compression plate 32 corresponding to the protruding portion 52A of the acoustic matching member 50, the operator can easily recognize the imaging region of an ultrasound image (or the outside of the imaging region of an ultrasound image) based on a region where the upper acoustic matching member 62 is provided.

Thus, the acoustic matching members 50 to 56 used in the medical imaging apparatus 10 of the first and second embodiments are acoustic matching members located between the breast N and the compression plate 32. In addition, in the case of compressing the breast of the subject in contact with the compression plate 32, the protruding portions 50A to 56A that protrude toward the imaging table 31 disposed opposite to the compression plate 32 are provided in an end portion on the deepest side (nipple side) when viewed from the chest wall side of the subject.

In a space formed by the protruding portions 50A to 56A of the acoustic matching members 50 to 56 and the imaging table 31, the breast N is compressed by the compression plate 32. In the compression of the breast N, since the protruding portions 50A to 56A are in contact with the imaging table 31, excessive compression of the breast N can be suppressed. Therefore, since unnecessary deformation of the breast can be suppressed, it is possible to reduce the burden on the subject.

In the above first and second embodiments, the cases have been described in which the acoustic matching members 50 to 56 having the protruding portions 50A to 56A that protrude toward the imaging table 31 are disposed between the compression plate 32 and the breast N. In the second embodiment described above, however, the shape of the upper acoustic matching member disposed on the upper surface of the compression plate 32 may be a shape having a protruding portion that protrudes toward the imaging table 31. For example, as in an example shown in FIG. 16, an acoustic matching member 58 may be provided between the compression plate 32 and the breast N, and an upper acoustic matching member 64 may be provided on the upper surface of the compression plate 32.

As shown in FIG. 16, the acoustic matching member 58 is a rectangular parallelepiped in which a surface in contact with the compression plate 32 has the same shape and area as the bottom surface of the compression plate 32. On the other hand, the upper acoustic matching member 64 covers the upper surface of the compression plate 32, the side surface of the compression plate 32 on the nipple side, and the side surface of the acoustic matching member 58 on the nipple side, and has a protruding portion 64A that protrudes toward the imaging table 31 beyond the bottom surface of the acoustic matching member 58.

Thus, in a case where the upper acoustic matching member 64 has the protruding portion 64A that protrudes toward the imaging table 31 beyond the bottom surface of the acoustic matching member 58, the breast N is compressed by the compression plate 32 in a space formed by the acoustic matching member 58, the protruding portion 64A of the upper acoustic matching member 64, and the imaging table 31. Also in the present embodiment, the upper acoustic matching member 64 has the protruding portion 64A. Therefore, in the same manner as in the embodiment described above, since excessive compression of the breast N can be suppressed, it is possible to reduce the burden on the subject.

Third Embodiment

Next, a third embodiment will be described. The same portions as in the medical imaging apparatus 10 and the acoustic matching member of each embodiment described above are denoted by the same reference numerals, and the detailed explanation thereof will be omitted.

Since the configuration of the medical imaging apparatus 10 is the same as that of the medical imaging apparatus 10 (refer to FIGS. 1 and 2) of the first embodiment, the explanation thereof will be omitted.

In the medical imaging apparatus 10 of the present embodiment, similar to the medical imaging apparatus 10 of the second embodiment described above, in the case of capturing an ultrasound image, an acoustic matching member is provided between the compression plate 32 and the breast N, and an upper acoustic matching member is provided on the upper surface of the compression plate 32.

Therefore, the overall flow of a series of imaging operations in the case of performing imaging in the continuous imaging mode in the medical imaging apparatus 10 of the present embodiment is the same as the overall flow (refer to FIG. 14) of the imaging operation of the second embodiment. In addition, breast compression processing in the medical imaging apparatus 10 of the present embodiment is the same as the breast compression processing (refer to FIG. 6) of the first embodiment.

In the medical imaging apparatus 10 of the present embodiment, the type of an acoustic matching member provided between the compression plate 32 and the breast N may be different from the type of an upper acoustic matching member provided on the upper surface of the compression plate 32, and the shapes of the acoustic matching member and the upper acoustic matching member are not limited to the shapes exemplified in the first and second embodiments described above. Hereinafter, the shapes of the acoustic matching member and the upper acoustic matching member in the present embodiment will be described by way of examples.

Example 3-1

Figure 17:
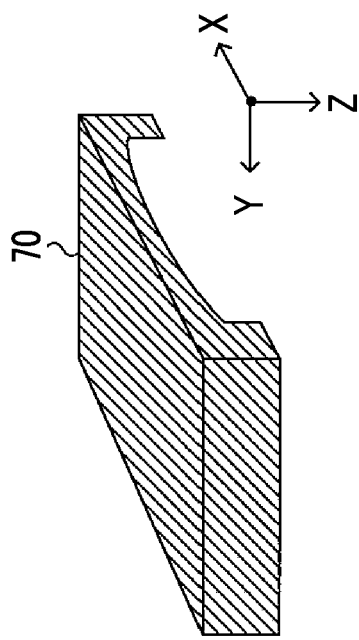
FIG. 17 is a perspective view of an acoustic matching member of Example 3-1 in a third embodiment.
Figure 18:
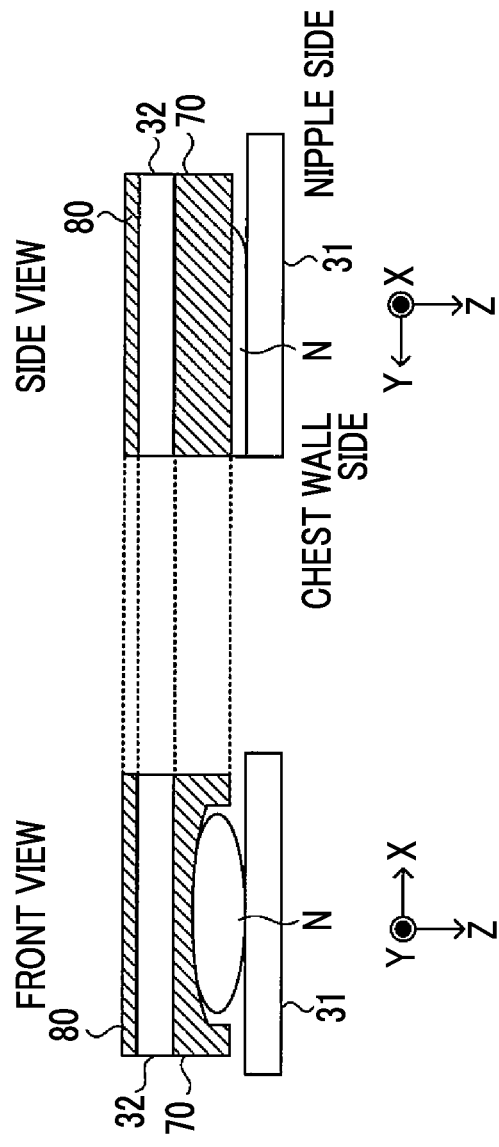
FIG. 18 is a front view when a state, in which a compression plate compresses a breast with the acoustic matching member shown in FIG. 17 interposed between the compression plate and the breast, is viewed from the direction of the nipple of the breast and a side view when the state is viewed from the side surface of the subject.

FIG. 17 shows a perspective view of an acoustic matching member 70 of this example, and FIG. 18 shows a front view when a state, in which the compression plate 32 compresses the breast N with the acoustic matching member 70 interposed between the compression plate 32 and the breast N, is viewed from the direction of the nipple of the breast N and a side view when the state is viewed from the side surface of the subject.

As shown in FIGS. 17 and 18, in the acoustic matching member 70 of this example, the thickness of a portion in contact with the breast N changes along the X-axis direction. Specifically, as shown in FIGS. 17 and 18, in the acoustic matching member 70 of this example, the shape of a portion in contact with the breast N is a recessed shape that is recessed toward the central portion from the end portion in the horizontal direction of the subject.

The acoustic matching member 70 of this example is the same as the acoustic matching member 54 (refer to FIG. 10) of Example 1-3 of the first embodiment in that the shape of a portion in contact with the breast is a recessed shape that is recessed toward the central portion from the end portion in the horizontal direction of the subject, but is different from the acoustic matching member 54 (refer to FIG. 10) of Example 1-3 of the first embodiment in that a protruding portion corresponding to the protruding portion 54A provided in the acoustic matching member 54 is provided.

Therefore, as shown in FIGS. 17 and 18, the shape of the acoustic matching member 70 of this example when viewed from the direction of the nipple of the breast N is a recessed shape that is recessed toward the central portion from the end portion in the horizontal direction of the subject.

In addition, as shown in FIG. 18, an upper acoustic matching member 80 of this example is a rectangular parallelepiped in which a surface in contact with the compression plate 32 has the same area as the bottom surface of the compression plate 32.

As described above in Example 1-3 of the first embodiment, in general, the thickness of the breast N in the horizontal direction of the subject increases toward the nipple portion and decreases toward the left and right end portions of the subject. Therefore, by forming the acoustic matching member 70 in the shape shown in FIGS. 17 and 18, it is possible to perform compression according to the shape of the breast N. As a result, it is possible to reduce the compression pressure applied to the chest wall side. Thus, according to the acoustic matching member 70 of this example, it is possible to reduce the burden on the subject at the time of compression using the compression plate 32.

Example 3-2

Figure 19:
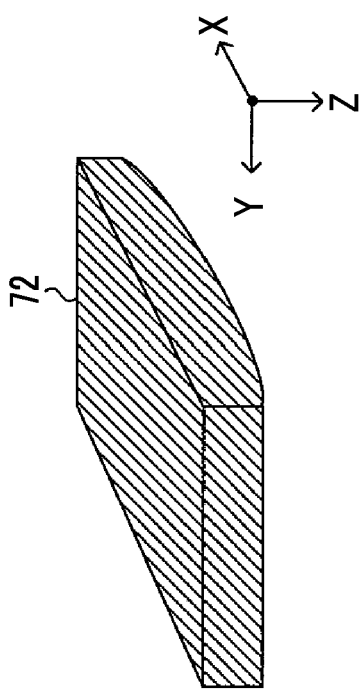
FIG. 19 is a perspective view of an acoustic matching member of Example 3-2 in the third embodiment.
Figure 20:
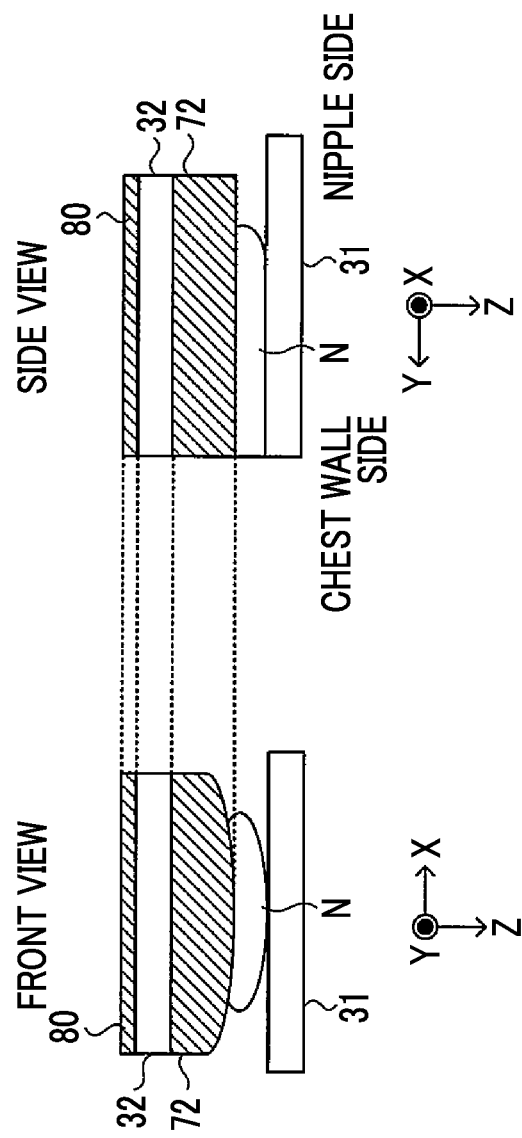
FIG. 20 is a front view when a state, in which a compression plate compresses a breast with the acoustic matching member shown in FIG. 19 interposed between the compression plate and the breast, is viewed from the direction of the nipple of the breast and a side view when the state is viewed from the side surface of the subject.

FIG. 19 shows a perspective view of an acoustic matching member 72 of this example, and FIG. 20 shows a front view when a state, in which the compression plate 32 compresses the breast N with the acoustic matching member 72 interposed between the compression plate 32 and the breast N, is viewed from the direction of the nipple of the breast N and a side view when the state is viewed from the side surface of the subject.

As shown in FIGS. 19 and 20, in the acoustic matching member 72 of this example, the thickness of a portion in contact with the breast N changes along the X-axis direction. Specifically, in the acoustic matching member 72 of this example, as shown in FIGS. 19 and 20, the shape of a portion in contact with the breast N is a protruding shape that protrudes toward the imaging table 31, and the thickness of a portion of the acoustic matching member 56 in contact with the breast N is the largest in the central portion of the compression plate 32 in the X-axis direction and is the smallest in the end portion of the compression plate 32 in the X-axis direction.

The acoustic matching member 72 of this example is the same as the acoustic matching member 56 (refer to FIG. 11) of Example 1-4 of the first embodiment in that the shape of a portion in contact with the breast is a protruding shape that protrudes toward the imaging table 31, but is different from the acoustic matching member 56 (refer to FIG. 11) of Example 1-4 of the first embodiment in that there is no protruding portion corresponding to the protruding portion 56A provided in the acoustic matching member 56.

Therefore, as shown in FIGS. 19 and 20, the shape of the acoustic matching member 72 of this example when viewed from the direction of the nipple of the breast N is a protruding shape that protrudes toward the imaging table 31.

The upper acoustic matching member 80 provided on the upper surface of the compression plate 32 is the same as that in Example 3-1 described above.

As described above in Example 1-4 of the first embodiment, in general, the thickness of the breast N in the horizontal direction of the subject increases toward the nipple portion and decreases toward the left and right end portions of the subject. Therefore, in order to make the breast N uniform in thickness, it is preferable to compress the nipple portion more than the left and right end portions. By forming the acoustic matching member 72 in the shape shown in FIGS. 19 and 20, it is possible to increase the compression pressure toward the nipple portion of the breast N. As a result, it becomes easy to make the thickness of the breast N uniform.

Example 3-3

Figure 21:
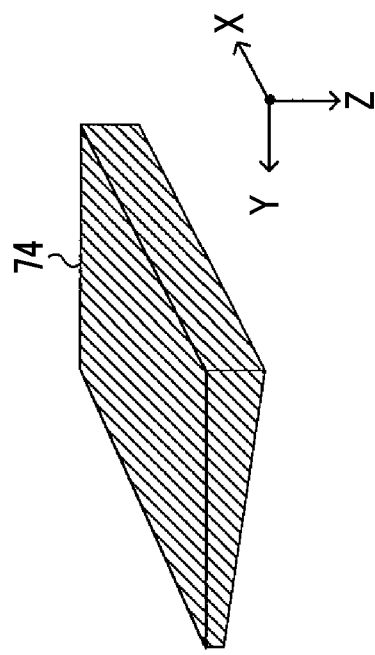
FIG. 21 is a perspective view of an acoustic matching member of Example 3-3 in the third embodiment.
Figure 22:
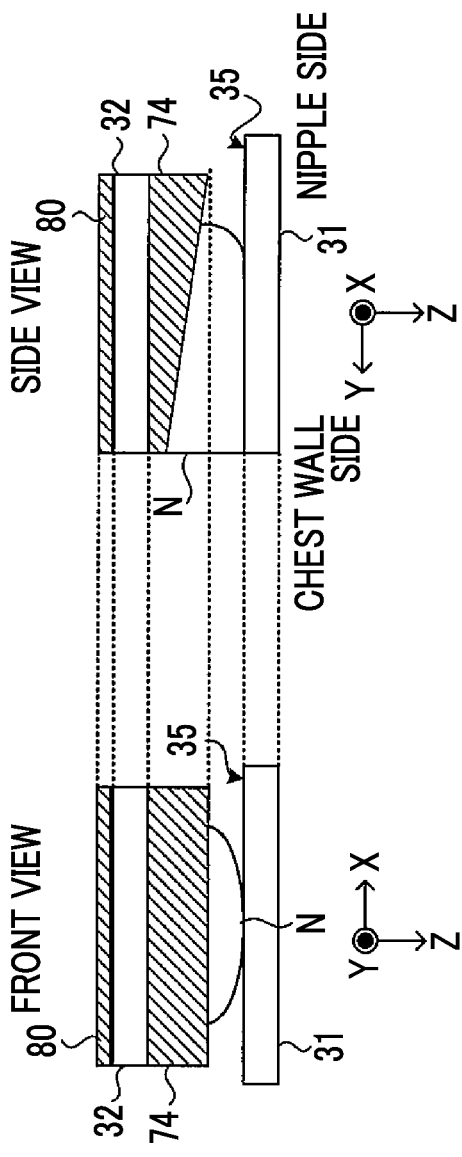
FIG. 22 is a front view when a state, in which a compression plate compresses a breast with the acoustic matching member shown in FIG. 21 interposed between the compression plate and the breast, is viewed from the direction of the nipple of the breast and a side view when the state is viewed from the side surface of the subject.

FIG. 21 shows a perspective view of an acoustic matching member 74 of this example, and FIG. 22 shows a front view when a state, in which the compression plate 32 compresses the breast N with the acoustic matching member 74 interposed between the compression plate 32 and the breast N, is viewed from the direction of the nipple of the breast N and a side view when the state is viewed from the side surface of the subject.

As shown in FIGS. 21 and 22, in the acoustic matching member 74 of this example, the thickness of a portion in contact with the breast N changes along the Y-axis direction. Specifically, as shown in FIGS. 21 and 22, in the acoustic matching member 74 of this example, the thickness of a portion in contact with the breast N is the smallest on the chest wall side and the largest on the nipple side.

The upper acoustic matching member 80 provided on the upper surface of the compression plate 32 is the same as that in Example 3-1 described above.

As described above in Example 1-2 of the first embodiment, in general, the thickness of the breast N in the vertical direction of the subject increases toward the chest wall side and decreases toward the nipple side. Therefore, by forming the acoustic matching member 74 in the shape shown in FIGS. 21 and 22, it is possible to perform compression according to the shape of the breast N. As a result, it is possible to reduce the compression pressure applied to the chest wall side. Thus, according to the acoustic matching member 74 of this example, it is possible to reduce the burden on the subject at the time of compression using the compression plate 32.

Example 3-4

Figure 23:
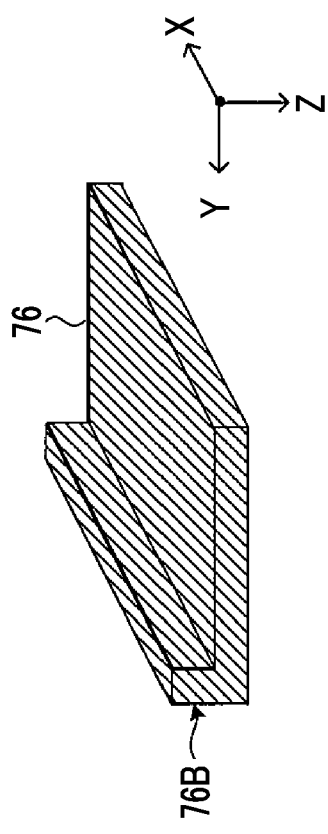
FIG. 23 is a perspective view of an acoustic matching member of Example 3-4 in the third embodiment.
Figure 24:
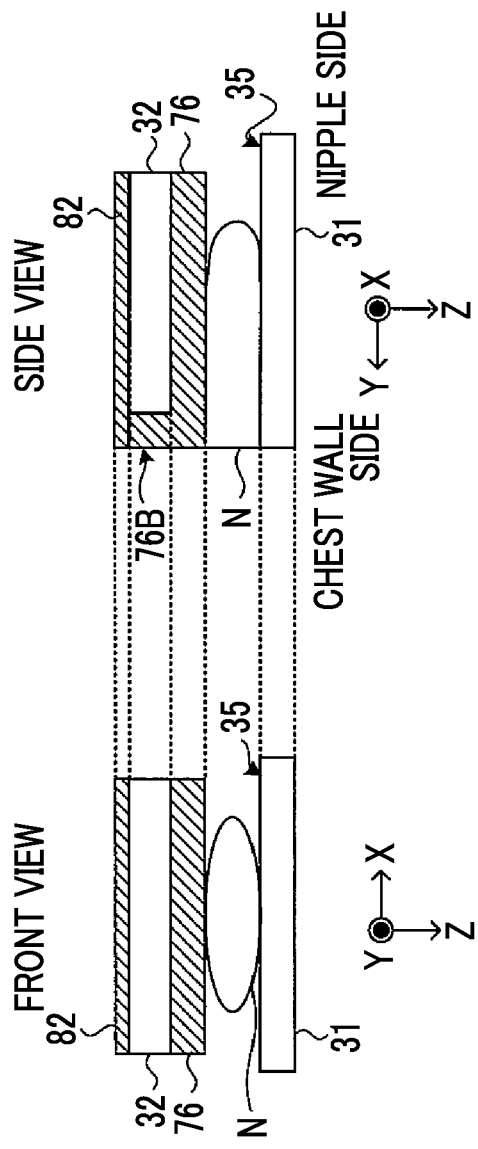
FIG. 24 is a front view when a state, in which a compression plate compresses a breast with the acoustic matching member shown in FIG. 23 interposed between the compression plate and the breast, is viewed from the direction of the nipple of the breast and a side view when the state is viewed from the side surface of the subject.

FIG. 23 shows a perspective view of an acoustic matching member 76 of this example, and FIG. 24 shows a front view when a state, in which the compression plate 32 compresses the breast N with the acoustic matching member 76 interposed between the compression plate 32 and the breast N, is viewed from the direction of the nipple of the breast N and a side view when the state is viewed from the side surface of the subject.

As shown in FIGS. 23 and 24, in the acoustic matching member 76 of this example, on the chest wall side of the breast N, a protruding portion 76B that protrudes in a direction away from the imaging table 31 is provided along the side surface of the compression plate 32. In the present embodiment, the height of the protruding portion 76B is set to a height corresponding to the thickness of the compression plate 32.

As shown in FIG. 24, an upper acoustic matching member 82 of this example is a rectangular parallelepiped having a contact surface in contact with the compression plate 32 and the protruding portion 76B of the acoustic matching member 76.

Since the acoustic matching member 76 of this example has the protruding portion 76B in contact with the side surface of the compression plate 32, it is sufficient to match the shape of the compression plate 32 in a case where the operator performs positioning of the acoustic matching member 76. Accordingly, the positioning becomes easy.

Example 3-5

Figure 25:
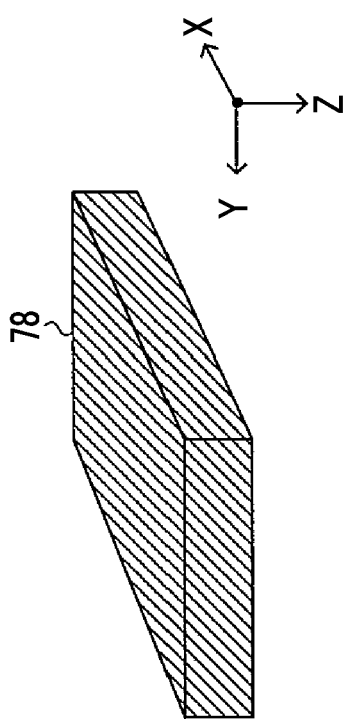
FIG. 25 is a perspective view of an acoustic matching member of Example 3-5 in the third embodiment.
Figure 26:
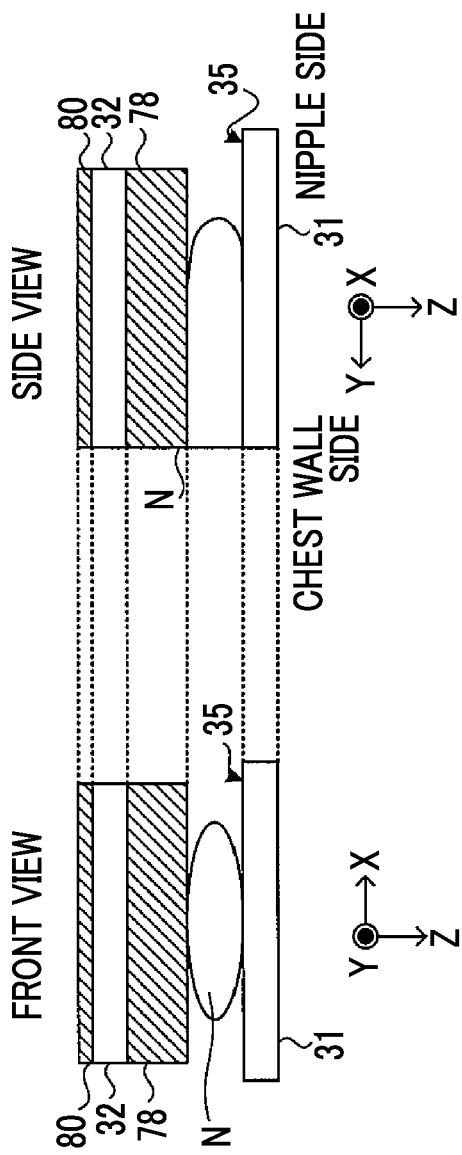
FIG. 26 is a front view when a state, in which a compression plate compresses a breast with the acoustic matching member shown in FIG. 25 interposed between the compression plate and the breast, is viewed from the direction of the nipple of the breast and a side view when the state is viewed from the side surface of the subject.

FIG. 25 shows a perspective view of an acoustic matching member 78 of this example, and FIG. 26 shows a front view when a state, in which the compression plate 32 compresses the breast N with the acoustic matching member 78 interposed between the compression plate 32 and the breast N, is viewed from the direction of the nipple of the breast N and a side view when the state is viewed from the side surface of the subject.

As shown in FIGS. 25 and 26, the acoustic matching member 78 of this example is a rectangular parallelepiped having a surface in contact with the compression plate 32, the surface having the same area as the bottom surface of the compression plate 32. The upper acoustic matching member 80 provided on the upper surface of the compression plate 32 is the same as that in Example 3-1 described above.

In the acoustic matching member 78 and the upper acoustic matching member 80, the thickness of the acoustic matching member 78 in the Z-axis direction is larger than the thickness of the upper acoustic matching member 80 in the Z-axis direction.

As described above in Example 1-1 of the first embodiment, the acoustic matching member 78 preferably has high adhesion to the breast N, and the upper acoustic matching member 80 preferably has high lubricity in order to move the ultrasound probe 36 smoothly. Therefore, the static friction coefficient of the acoustic matching member 78 is larger than the static friction coefficient of the upper acoustic matching member 80.

For the hardness of the acoustic matching member 78, it is preferable that, in the Y-axis direction, the hardness on the chest wall side of the breast N is lower than the hardness on the nipple side (in other words, the acoustic matching member 78 on the chest wall side of the breast N is softer than the acoustic matching member 78 on the nipple side). In this case, since the acoustic matching member 78 tends to be deformed on the chest wall side compared with the nipple side, the acoustic matching member 78 is likely to be deformed according to the shape of the breast N. Therefore, it is possible to reduce the burden on the subject.

Thus, in the acoustic matching members 70 to 78 used in the medical imaging apparatus 10 of the third embodiment, there are provided: the acoustic matching members 70 to 78 which are provided on the bottom surface of the compression plate 32 on the breast N side in the case of compressing the breast N of the subject with the compression plate 32; and the upper acoustic matching members 80 and 82 which are provided on the upper surface on the opposite side to the bottom surface of the compression plate 32 in the case of compressing the breast N with the compression plate 32 and whose types are different from the acoustic matching members 70 to 78.

In the present embodiment, since the type of the acoustic matching member provided on the bottom surface of the compression plate 32 is different from the type of the upper acoustic matching member provided on the upper surface of the compression plate 32, it is possible to use an appropriate acoustic matching member and an appropriate upper acoustic matching member. Therefore, according to the present embodiment, in the case of capturing an ultrasound image of the breast N of the subject in a state in which the breast N is compressed by the compression plate 32, it is possible to reduce the burden on the subject.

In the above second and third embodiments, the cases have been described in which the upper acoustic matching members 60, 62, 80, and 82 in the so-called gel sheet form are provided on the upper surface of the compression plate 32. However, the upper acoustic matching member provided on the upper surface of the compression plate 32 is not limited to the gel sheet form. For example, the upper acoustic matching member may be a volatile lubricant. Thus, by using the upper acoustic matching member that is a gel sheet form or a volatile lubricant, it becomes easy to place the upper acoustic matching member on the upper surface of the compression plate 32 compared with a case of using so-called echogenic jelly, which requires application and removal onto and from the upper surface of the compression plate 32.

In each of the above embodiments, the case has been described in which the medical imaging apparatus 10 has a function of capturing a radiographic image and a function of capturing an ultrasound image. However, without being limited thereto, the medical imaging apparatus 10 may have at least a function of capturing an ultrasound image. In a general mammography apparatus, in the case of capturing a radiographic image of the breast N, the breast N of the subject is compressed by the compression plate. On the other hand, in the case of capturing an ultrasound image of the breast N using a general ultrasound imaging apparatus, the operator moves the ultrasound probe on the surface of the breast N of the subject to perform imaging. Thus, in the case of capturing a radiographic image and the case of capturing an ultrasound image, the compression state of the breast N of the subject, the state of imaging, and the like are different. For this reason, in the case of comparing both the images, it may be difficult to observe a region of interest. In contrast, as in the medical imaging apparatus 10 of the present embodiment, by providing a function of capturing a radiographic image and a function of capturing an ultrasound image, it is possible to suppress differences in the compression state of the breast N of the subject, the state of imaging, and the like in the case of capturing a radiographic image and the case of capturing an ultrasound image. Therefore, according to the medical imaging apparatus 10 of the present embodiment, the user can easily compare the radiographic image and the ultrasound image with each other.

The radiation R in each of the above embodiments is not particularly limited, and X-rays, γ-rays, and the like can be applied.

The configuration, operation, and the like of the medical imaging apparatus 10 described in each of the above embodiments are examples, and it is needless to say that these can be changed according to the circumstances within the scope not deviating from the spirit of the invention.

For the above embodiments, the following additional notes are disclosed.

(Note 1)

An acoustic matching member group, comprising: a first acoustic matching member that is provided on a first surface of a compression plate on a breast side in a case of compressing the breast of a subject with the compression plate; and a second acoustic matching member that is provided on a second surface of the compression plate on a side opposite to the first surface in a case of compressing the breast with the compression plate and that is of a different type from the first acoustic matching member.

(Note 2)

In the acoustic matching member group described in Note 1, a static friction coefficient of the first acoustic matching member is larger than a static friction coefficient of the second acoustic matching member.

(Note 3)

In the acoustic matching member group described in Note 1 or 2, a thickness of the first acoustic matching member is larger than a thickness of the second acoustic matching member in a compression direction of the compression plate.

(Note 4)

In the acoustic matching member group described in any one of Notes 1 to 3, a hardness of the first acoustic matching member on a chest wall side of the subject is lower than a hardness of the first acoustic matching member on a nipple side of the subject.

(Note 5)

In the acoustic matching member group described in any one of Notes 1 to 4, a surface of the first acoustic matching member in contact with the breast of the subject has a recessed shape that is recessed toward a central portion from an end portion in a horizontal direction of the subject.

(Note 6)

In the acoustic matching member group described in any one of Notes 1 to 4, the first acoustic matching member has a protruding shape that protrudes toward the imaging table.

(Note 7)

A medical imaging apparatus, comprising: the acoustic matching member group described in any one of Notes 1 to 6; an imaging table on which the breast of the subject is placed; a compression plate that compresses the breast in contact with the acoustic matching member group; and an ultrasound imaging unit that captures an ultrasound image of the breast.

(Note 8)

The medical imaging apparatus described in Note 7, further comprising: a radiographic imaging unit that captures a radiographic image of the breast.

What is claimed is:

1. An acoustic matching member group, comprising:
   an acoustic matching member configured to be disposed between a breast placed on an imaging table and a compression plate disposed opposite to the imaging table, the acoustic matching member comprising:
   a protruding portion configured such that that protrudes toward the imaging table and that is provided in an end portion on a deepest side when viewed from a chest wall side of a subject in a case of compressing a breast of the subject in contact with the compression plate; and
   an upper acoustic matching member provided on a surface of the compression plate opposite to a surface facing the imaging table configured for compressing the breast of the subject in contact with the compression plate,
   wherein a static friction coefficient of the acoustic matching member is larger than a static friction coefficient of the upper acoustic matching member.

2. The acoustic matching member group according to claim 1,
   wherein a thickness of the acoustic matching member on the chest wall side of the subject is smaller than that in the end portion on the deepest side.

3. The acoustic matching member group according to claim 1,
   wherein a surface configured to be in contact with the breast of the subject has a recessed shape that is recessed toward a central portion from an end portion in a horizontal direction of the subject.

4. The acoustic matching member group according to claim 1,
   wherein the acoustic matching member has a protruding shape that protrudes toward the imaging table.

5. The acoustic matching member group according to claim 1,
   wherein the acoustic matching member configured to have a higher hardness than a hardness set in advance as a hardness of the breast.

6. The acoustic matching member group according to claim 1,
   wherein a thickness of the acoustic matching member in a compression direction of the compression plate is larger than a thickness of the upper acoustic matching member.

7. The acoustic matching member group according to claim 1,
   wherein the upper acoustic matching member is provided in a region of the compression plate other than a region corresponding to the protruding portion.

8. A medical imaging apparatus, comprising:
   the acoustic matching member group according to claim 1;
   an imaging table configured for placement of the breast of the subject;
   a compression plate configured such that is compresses the breast in contact with the acoustic matching member;
   an ultrasound probe configured to scans the breast of the subject with ultrasound waves to acquire an ultrasound image of the breast; and
   a processor that is configured to control the ultrasound probe to capture an ultrasound image of the breast.

9. The medical imaging apparatus according to claim 8, further comprising:
   a contact sensor that detects contact of the protruding portion of the acoustic matching member with the imaging table; and
   wherein the processor is further configured to control the compression plate to reduce a compression pressure of the breast by the compression plate such that the contact sensor detects contact of the protruding portion while the compression plate is compressing the breast.

10. A medical imaging apparatus, comprising:
    the acoustic matching member group according to claim 1;
    an imaging table configured for placement of the breast of the subject;
    a compression plate configured such that is compresses the breast in contact with the acoustic matching member group;
    an ultrasound probe configured to scans the breast of the subject with ultrasound waves to acquire an ultrasound image of the breast; and
    a processor that is configured to control the ultrasound probe to capture an ultrasound image of the breast.

11. The medical imaging apparatus according to claim 8, further comprising:
    a radiation emitter that emits radiation; and
    a radiation detector configured to detect radiation transmitted through the breast;
    wherein the processor is further configured to control the radiation emitter and the radiation detector to capture a radiographic image of the breast.

* * * * *